US008242227B2

(12) United States Patent
Guo et al.

(10) Patent No.: US 8,242,227 B2
(45) Date of Patent: Aug. 14, 2012

(54) DOPED POLYSILANES, COMPOSITIONS CONTAINING THE SAME, METHODS FOR MAKING THE SAME, AND FILMS FORMED THEREFROM

(75) Inventors: Wenzhuo Guo, Cupertino, CA (US); Vladimir K. Dioumaev, Mountain View, CA (US); Joerg Rockenberger, Redwood City, CA (US)

(73) Assignee: Kovio, Inc., San Jose, CA (US)

( * ) Notice: Subject to any disclaimer, the term of this patent is extended or adjusted under 35 U.S.C. 154(b) by 0 days.

(21) Appl. No.: 13/093,273

(22) Filed: Apr. 25, 2011

(65) Prior Publication Data

US 2011/0197783 A1 Aug. 18, 2011

Related U.S. Application Data

(62) Division of application No. 11/249,167, filed on Oct. 11, 2005, now Pat. No. 7,951,892.

(60) Provisional application No. 60/617,562, filed on Oct. 8, 2004.

(51) Int. Cl.
*C08G 77/00* (2006.01)

(52) U.S. Cl. ............... 528/31; 528/5; 528/33; 528/398

(58) Field of Classification Search ........................ None
See application file for complete search history.

(56) References Cited

U.S. PATENT DOCUMENTS

| | | | |
|---|---|---|---|
| 4,052,430 A | 10/1977 | Yajima et al. |
| 4,276,424 A | 6/1981 | Peterson, Jr. et al. |
| 4,310,482 A | 1/1982 | Baney |
| 4,537,942 A | 8/1985 | Brown-Wensley et al. |
| 4,554,180 A | 11/1985 | Hirooka |
| 4,611,035 A | 9/1986 | Brown-Wensley et al. |
| 4,683,145 A | 7/1987 | Nishimura et al. |
| 4,683,146 A | 7/1987 | Hirai et al. |
| 4,704,444 A | 11/1987 | Brown-Wensley et al. |
| 4,726,963 A | 2/1988 | Ishihara et al. |
| 4,759,947 A | 7/1988 | Ishihara et al. |
| 4,820,788 A | 4/1989 | Zeigler |
| 4,822,703 A | 4/1989 | Badesha et al. |
| 4,830,890 A | 5/1989 | Kanai |
| 4,835,005 A | 5/1989 | Hirooka et al. |
| 4,841,083 A | 6/1989 | Nagai et al. |
| 4,992,520 A | 2/1991 | Zeigler |
| 5,153,295 A | 10/1992 | Whitmarsh et al. |
| 5,204,380 A | 4/1993 | Seyferth et al. |
| 5,358,987 A | 10/1994 | Kanai et al. |
| 5,700,400 A | 12/1997 | Ikai et al. |
| 5,798,428 A | 8/1998 | Schwab et al. |
| 5,866,471 A | 2/1999 | Beppu et al. |
| 5,942,637 A | 8/1999 | Boudjouk et al. |
| 6,005,036 A | 12/1999 | Carrozza et al. |
| 6,140,448 A | 10/2000 | Choi et al. |
| 6,174,982 B1 | 1/2001 | Nishida et al. |
| 6,503,570 B2 | 1/2003 | Matsuki et al. |
| 6,514,801 B1 | 2/2003 | Yudasaka et al. |
| 6,517,911 B1 | 2/2003 | Matsuki |
| 6,518,087 B1 | 2/2003 | Furusawa et al. |
| 6,527,847 B1 | 3/2003 | Matsuki |
| 6,541,354 B1 | 4/2003 | Shimoda et al. |
| 6,610,872 B1 | 8/2003 | Choi et al. |
| 6,767,775 B1 | 7/2004 | Yudasaka et al. |
| 6,846,513 B2 | 1/2005 | Furusawa et al. |
| 6,884,700 B2 | 4/2005 | Aoki et al. |
| 6,908,796 B2 | 6/2005 | Furusawa |

(Continued)

FOREIGN PATENT DOCUMENTS

CN 1297578 A 5/2001

(Continued)

OTHER PUBLICATIONS

Dioumaev, Vladimir K. and Harrod, John F.; "A Systematic Analysis of the Structure-Reactivity Trends for Some 'Cation-like' Early Transition Metal Catalysts for Dehydropolymerization of Silanes"; Jan. 10, 1996; pp. 133-143; Journal of Organometallic Chemistry 521; Elsevier Science S.A.; Canada.

Feher, F., Plichta, P., and Guillery, R.; "Beitrage Zur Chemie Des Siliciums Und Germaniums Xlll1—Uber Die Darstellung Neuer Phenylsilane" May 13, 1970; pp. 2889-2893; Tetrahedron Letters No. 33; Pergamon Press; Great Britain.

Feher, F., Plichta, P., and Guillery, R.; "Beitrage Zur Chemie Des Siliziums Und Germaniums XIV1—Uber Die Umsetzung Von Kaliumsilyl Mit Phenylbromsilanen und Phenylbromgermanen Darstellung Von Phenylsilylkalium" Sep. 15, 1970; pp. 4443-4447; Tetrahedron Letters No. 51; Pergamon Press; Great Britain.

Hassler, Karl and Koll, Wolfgang; "Synthese Und Eigenschaften Chlorierter Und Bromierter Aryltrisilane und Aryltetrasilane"; Oct. 2, 1996; pp. 135-143; Journal of Organometallic Chemistry 538; Elsevier Science S.A.; Canada.

(Continued)

*Primary Examiner* — Marc Zimmer
(74) *Attorney, Agent, or Firm* — The Law Offices of Andrew D. Fortney, Ph.D., P.C.; Andrew D. Fortney; Sharon E. Brown Turner (57) ABSTRACT

Doped polysilanes, inks containing the same, and methods for their preparation and use are disclosed. The doped polysilane generally has the formula $H-[A_aH_b(DR_x)_m]_q-[(A_cH_dR^1_e)_n]_p-H$, where each instance of A is independently Si or Ge, and D is B, P, As or Sb. In preferred embodiments, R is H, $-A_fH_{f+1}R^2_f$, alkyl, aryl or substituted aryl, and $R^1$ is independently H, halogen, aryl or substituted aryl. In one aspect, the method of making a doped poly(aryl)silane generally includes the steps of combining a doped silane of the formula $A_aH_{b+2}(DR_x)_m$ (optionally further including a silane of the formula $A_cH_{d+2}R^1_e$) with a catalyst of the formula $R^4_wR^5_yMX_z$ (or an immobilized derivative thereof) to form a doped poly(aryl)silane, then removing the metal M. In another aspect, the method of making a doped polysilane includes the steps of halogenating a doped polyarylsilane, and reducing the doped halopolysilane with a metal hydride to form the doped polysilane. The synthesis of semiconductor inks via dehydrocoupling of doped silanes and/or germanes allows for tuning of the ink properties (e.g., viscosity, boiling point, surface tension and dopant level or concentration) and for deposition of doped silicon films or islands by spincoating, inkjetting, dropcasting, etc., with or without the use of UV irradiation.

45 Claims, 6 Drawing Sheets

U.S. PATENT DOCUMENTS

| | | | |
|---|---|---|---|
| 7,052,980 | B2 | 5/2006 | Aoki |
| 7,067,069 | B2 | 6/2006 | Shiho et al. |
| 7,078,276 | B1 | 7/2006 | Zurcher et al. |
| 7,223,802 | B2 | 5/2007 | Aoki et al. |
| 2001/0021760 | A1 | 9/2001 | Matsuki et al. |
| 2003/0045632 | A1 | 3/2003 | Shiho et al. |
| 2003/0087110 | A1 | 5/2003 | Furusawa et al. |
| 2003/0148024 | A1 | 8/2003 | Kodas et al. |
| 2003/0229190 | A1 | 12/2003 | Aoki et al. |
| 2004/0029364 | A1 | 2/2004 | Aoki et al. |
| 2004/0248429 | A1 | 12/2004 | Aoki |
| 2005/0176183 | A1 | 8/2005 | Aoki |
| 2005/0181566 | A1 | 8/2005 | Machida et al. |
| 2006/0159859 | A1 | 7/2006 | Iwasawa |
| 2006/0185712 | A1 | 8/2006 | Shiho et al. |
| 2006/0198966 | A1 | 9/2006 | Kaino et al. |
| 2007/0190265 | A1 | 8/2007 | Aoki et al. |
| 2009/0215920 | A1 | 8/2009 | Iwasawa et al. |

FOREIGN PATENT DOCUMENTS

| | | |
|---|---|---|
| CN | 1407018 A | 4/2003 |
| DE | 3122992 A1 | 2/1982 |
| EP | 1085560 A1 | 3/2001 |
| EP | 1085579 A1 | 3/2001 |
| EP | 1087428 A1 | 3/2001 |
| EP | 1087433 A1 | 3/2001 |
| EP | 1113502 A1 | 7/2001 |
| EP | 0902030 B1 | 10/2002 |
| EP | 1284306 A2 * | 2/2003 |
| EP | 1357154 A1 | 10/2003 |
| GB | 2077710 A | 12/1981 |
| JP | 57-27915 A | 2/1982 |
| JP | 60-242612 A | 12/1985 |
| JP | 4-334551 A | 11/1992 |
| JP | 5-230219 A | 9/1993 |
| JP | 6-191821 A | 7/1994 |
| JP | 7-267621 A | 10/1995 |
| JP | 9-45922 A | 2/1997 |
| JP | 9-237927 A | 9/1997 |
| JP | 11-79727 A | 3/1999 |
| JP | 11-171528 A | 6/1999 |
| JP | 2000-7317 A | 1/2000 |
| JP | 2000-31066 A | 1/2000 |
| JP | 2002-203794 A | 7/2002 |
| JP | 2002-246384 A | 8/2002 |
| JP | 2003-55556 A | 2/2003 |
| JP | 2003-92297 A | 3/2003 |
| JP | 2003-124486 A | 4/2003 |
| JP | 2003-313299 A | 11/2003 |
| JP | 2003-318120 A | 11/2003 |
| JP | 2004-311945 A | 11/2004 |
| JP | 2005-219981 A | 8/2005 |
| WO | 00/59014 A1 | 10/2000 |
| WO | 00/59022 A1 | 10/2000 |
| WO | 00/59041 A1 | 10/2000 |
| WO | 2004/110929 A1 | 12/2004 |

OTHER PUBLICATIONS

Hassler, Karl, Katzenbeisser, Ulrike, and Reiter, Barbara; "Verbesserte Synthesen von Phenyltrisilanen"; Nov. 29, 1993; pp. 193-196; Journal of Organometallic Chemistry 479; Elsevier Science S.A.; Canada.

Hengge, E. and Firgo, H.; "An Electrochemical Method for the Synthesis of Silicon—Silicon Bonds"; Dec. 19, 1980; pp. 155-161; Journal of Organometallic Chemistry 212; Elsevier Sequoia S.A.; Netherlands.

Herzog, Uwe and West, Robert; "Heterosubstituted Polysilanes"; Feb. 9, 1999; pp. 2210-2214; Macromolecules 1999 No. 32; American Chemical Society; Worldwide Web.

Miller, Robert D. and Michl, Josef; "Polysilane High Polymers"; Mar. 27, 1989; pp. 1359-1410; Chem. Rev. 1989 vol. 89, No. 6; American Chemical Society; United States.

Miller, R. D. and Jenkner, P. K.; "Sacrificial Additives in the Wurtz Synthesis of Polysilanes"; Jan. 20, 1994; pp. 5921-5923; Macromolecules 1994, vol. 27, No. 20; American Chemical Society; United States.

Miller, R. D. and Sooriyakumaran, R.; "Soluble Alkyl Substituted Polygermanes: Thermochromic Behavior"; 1987; pp. 111-125; Journal of Polymer Science: Part A: Polymer Chemistry, vol. 25; John Wiley & Sons, Inc.; United States.

Miller, R. D., Thompson, D.; Sooriyakumaran, R., and Fickes, G. N.; "The Synthesis of Soluble, Substituted Silane High Polymers by Wurtz Coupling Techniques"; 1991; pp. 813-824; Journal of Polymer Science: Part A: Polymer Chemistry, vol. 29; John Wiley & Sons, Inc.; United States.

Richter, Robin, Gerhard, Roewer, Bohme, Uwe, Busch, Kathleen, Babonneau, Florence, Martin, Hans Peter, and Muller, Eberhard; "Organosilicon Polymers—Synthesis, Architecture, Reactivity and Applications"; Nov. 2, 1995; pp. 71-106; Applied Organometallic Chemistry, vol. 11; John Wiley & Sons, Ltd.; United States.

Shono, Tatsuya, Kashimura, Shigenori, and Murase, Hiroaki; "Electroreductive Systhesis of Polygermane and Germane—Silane Copolymer"; Mar. 24, 1992; pp. 896-897; J. Chem. Soc., Chem. Commun., 1992; Japan.

Tamao, Kohei, Kawachi, Atsushi, and Ito, Yoshihiko; "Coupling of (Amino)alkylchlorosilanes with Lithium: New Access to Symmetrical Di- and Tetrafunctional Alkyldisilanes"; Aug. 26, 1992; pp. 580-582; Organometallics 1993, vol. 12, No. 2; American Chemical Society; United States.

Tilley, Don T.; "The Coordination Polymerization of Silanes to Polysilanes by a "σ-Bond Metathesis" Mechanism. Implications for Linear Chain Growth"; Jul. 6, 1992; pp. 22-29; Acc. Chem. Res. 1993, vol. 26, No. 1; American Chemical Society; United States.

Uhlig, Wolfram; "Synthesis, Functionalization, and Cross-Linking Reactions of Organosilicon Polymers Using Silyl Triflate Inteimediates"; Aug. 23, 2001; pp. 255-305; Progress in Polymer Science, vol. 27; Elsevier Science Ltd.; Switzerland.

Uhlig, Wolfram; "Tailor-Made Synthesis of Functional Substituted Oligo- and Polysilanes from Silyl Triflates and (Aminosilyl)lithium Compounds"; Feb. 27, 2003; pp. 70-78; Journal of Organometallic Chemistry, vol. 685; Elsevier Science B.V.; Switzerland.

Wang, Qingzheng and Corey, Joyce Y.; "Dehydrocoupling Reactions of Hydrosilanes with Group 4 Metallocenes Cp2MY2 (M=Ti, Zr, Hf; Y=F, OPh, NMe2)"; Oct. 30, 2000; pp. 1434-1440; Can. J. Chem., vol. 78; NRC Research Press Website; Canada.

West, Robert; "The Polysilane High Polymers"; Sep. 19, 1985; pp. 327-346; Journal of Organometallic Chemistry, vol. 300; Elsevier Sequoia S.A.; Netherlands.

Takashi Aoki; "Method of Preparing Higher Order Silane Solution, Method of Forming Silicon Film, Silicon Film, Thin Film Transistor (TFT), and Electro-Optic Device"; Publication No. JP 2005219981 A; Publication Date: Aug. 18, 2005; Abstract from espacenet database, European Patent Office.

Takashi Aoki; "Method of Manufacturing Transistor, Electro-Optical Device and Electronic Apparatus"; Publication No. JP2004311945 A; Publication Date: Nov. 4, 2004; Abstract from espacenet database; European Patent Office.

Takashi Aoki, Masahiro Furusawa, and Kazuo Yudasaka; "Method for Manufacturing Device, Device and Electronic Apparatus"; Publication No. JP 2003318120 A; Publication Date: Nov. 7, 2003; Abstract from espacenet database; European Patent Office.

Takashi Aoki, Masahiro Furusawa, Yasuo Matsuki, Haruo Iwazawa, and Yasumasa Takeuchi; "Higher Order Silane Composition and Process for Forming Silicon Film Using the Same"; Publication No. JP2003313299 A; Publication Date: Nov. 6, 2003; Abstract from espacenet database; European Patent Office.

Kouji Shiho and Hitoshi Kato; "Production Method of Solar Cell and Composition Therefor"; Publication No. JP2003124486 A; Publication Date: Apr. 25, 2003; Abstract from espacenet database; European Patent Office.

Hitoshi Kato and Kouji Shiho; "Forming Method for Silicon Oxide Film and Composition for Formation"; Publication No. JP2003092297 A; Publication Date: Mar. 28, 2003; Abstract from espacenet database; European Patent Office.

Kouji Shiho and Hitoshi Kato; "Method for Forming Silicon Film or Silicon Oxide Film and Composition for Them"; Publication No. JP2003055556 A; Publication Date: Feb. 26, 2003; Abstract from espacenet database; European Patent Office.

Kouji Shiho and Hitoshi Kato; "Method of Forming Silicon Oxide Film and Composition Used for Forming the Same"; Publication No. JP2002246384 A; Publication Date: Aug. 30, 2002; Abstract from espacenet database; European Patent Office.

Masahiro Furusawa, Satoru Miyashita, Kazuo Yudasaka, Tatsuya Shimoda, Yasuaki Yokoyama, Yasuo Matsuki, and Yasumasa Takeuchi; "Formation Method of Silicon Thin Film"; Publication No. JP2002203794 A; Publication Date: Jul. 19, 2002; Abstract from espacenet database; European Patent Office.

Tsutomu Takadera, Keiichi Fukuyama, Akira Sakawaki, Kotaro Yano, and Yutaka Kitsuno; "Method for Forming Silicon Film and Manufacture of Solar Battery"; Publication No. JP2000031066 A; Publication Date: Jan. 28, 2000; Abstract from espacenet database; European Patent Office.

Keiichi Fukuyama, Tsutomu Takadera, and Masabumi Shimizu; "Formation of Silicon Film"; Publication No. JP2000007317 A; Publication Date: Jan. 11, 2000; Abstract from espacenet database; European Patent Office.

Raymond Philip Boudjouk, Beon-Kyu Kim, Michael P. Remington, and Bhanu Chauhan; "Tetradecachlorocyclohexasilane-Dianion-Containing Compound"; Publication No. JP11171528 A; Publication Date: Jun. 29, 1999; Abstract from espacenet database; European Patent Office.

Takashi Ouchida; "Formation of Silicon Film"; Publication No. JP11079727 A; Publication Date: Mar. 23, 1999; Abstract from espacenet database; European Patent Office.

Tatsuro Beppu, Shuji Hayase, Toshiro Hiraoka, Atsushi Kamata, and Kenji Sano; "Semiconductor Film Forming Method and Solar Cell Manufacturing Method"; Publication No. JP9237927 A; Publication Date: Sep. 9, 1997; Abstract from espacenet database; European Patent Office.

Yutaka Kitsuno, Kotaro Yano, Akira Sakawaki, and Keiji Kawasaki; "Method for Forming Poly Crystal Silicon Film"; Publication No. JP9045922 A; Publication Date: Feb. 14, 1997; Abstract from espacenet database; European Patent Office.

Kotaro Yano, Yutaka Kitsuno, Akira Sakawaki, and Keiji Kawasaki; "Formation of Silicon Membrane"; Publication No. JP7267621 A; Publication Date: Oct. 17, 1995; Abstract from espacenet database; European Patent Office.

Kotaro Yano, Yutaka Kitsuno, Shoichi Tazawa, and Keiji Kawasaki; "Higher Order Silane Containing Solution for Forming Silicon Film"; Publication No. JP6191821 A; Publication Date: Jul. 12, 1994; Abstract from espacenet database; European Patent Office.

Tamejirou Hiyama and Yasuo Hatanaka; "Production of Alpha, Omega-Dihydropolysilane"; Publication No. JP5230219 A; Publication Date: Sep. 7, 1993; Abstract from espacenet database; European Patent Office.

Ryuji Sato, Yasuo Nomura, Masashi Nakajima, and Yoshiharu Okumura; "Polymerization Catalyst of Hydrosilane"; Publication No. JP4334551 A; Publication Date: Nov. 20, 1992; Abstract from espacenet database; European Patent Office.

Yukio Nishimura, Hiroshi Matsuda, Masahiro Haruta, Yutaka Hirai, Takeshi Eguchi, and Takashi Katagiri; "Deposition Film Forming Method"; Publication No. JP60242612 A; Publication Date: Dec. 2, 1985; Abstract from espacenet database; European Patent Office.

Jiyon Fuiritsupu, Jiyon Toritsukaa Maikeru, and Jiyon Kingusuton Tooma Maikeru; "Synthesis of Polysilane"; Publication No. JP57027915 A; Publication Date: Feb. 15, 1982; Abstract from espacenet database; European Patent Office.

Shio Kooji and Katoo Nichika; "Silane Composition, Silicon Film Forming Method and Manufacture of Solar Cells"; Publication No. CN140718 A; Publication Date: Apr. 2, 2003; Abstract from espacenet database; European Patent Office.

Matsuki Yasuo; "Process for Formation of Silicon Oxide Films"; Publication No. CN1297578 A; Publication Date: May 30, 2001; Abstract from espacenet database; European Patent Office.

Phillip John, Michael John Tricker, and Michael John Kingston Thomas; "Process for Preparing Polysilane"; Publication No. DE3122992 A1; Publication Date: Feb. 4, 1982; Abstract from espacenet database; European Patent Office.

Haruo Iwasawa, Daohai Wang, Yasuo Matsuki, and Hitoshi Kato; "Silane Polymer and Method for Forming Silicon Film"; Publication No. WO2004110929 A1; Publication Date: Dec. 23, 2004; Abstract from espacenet database; European Patent Office.

Ichio Yudasaka, Tatsuya Shimoda, and Shunichi Seki; "Method of Manufacturing Thin-Film Transistor"; Publication No. WO0059041 A1; Publication Date: Oct. 5, 2000; Abstract from espacenet database; European Patent Office.

Yasuo Matsuki; "Process for the Formation of Silicon Oxide Films"; Publication No. WO0059022 A1; Publication Date: Oct. 5, 2000; Abstract from espacenet database; European Patent Office.

Shunichi Seki, Tatsuya Shimoda, Satoru Miyashita, Masahiro Furusawa, Ichio Yudasaka, Yasuo Matsuki, and Yasumasa Takeuchi; "Method for Forming a Silicon Film and Ink Composition for Ink Jet"; Publication No. WO0059014 A1; Publication Date: Oct. 5, 2000; Abstract from espacenet database; European Patent Office.

* cited by examiner

DOPED POLYSILANES, COMPOSITIONS CONTAINING THE SAME, METHODS FOR MAKING THE SAME, AND FILMS FORMED THEREFROM

RELATED APPLICATIONS

This application is a divisional of U.S. patent application Ser. No. 11/249,167, filed Oct. 11, 2005, now U.S. Pat. No. 7,951,892 which claims the benefit of U.S. Provisional Application No. 60/617,562, filed Oct. 8, 2004, which is incorporated herein by reference in its entirety. Furthermore, this application may be related to U.S. application Ser. No. 11/246,014, filed Oct. 6, 2005, which is incorporated herein by reference in its entirety.

FIELD OF THE INVENTION

The present invention generally relates to the field of doped polysilanes and methods of making the same. More specifically, embodiments of the present invention pertain to polysilane compounds containing dopant atoms, compositions containing the same, and methods for making and using the same.

SUMMARY OF THE INVENTION

Embodiments of the present invention relate to doped polysilanes, doped polysilane ink compositions, methods for making the same and methods of making an electrically active, semiconducting film using the same. The doped polysilanes generally have the formula $H-[A_aH_b(DR_x)_m]_q-[(A_cH_dR^1_e)_n]_p-H$, where each instance of A is independently Si or Ge; D is B, P, As or Sb; each instance of R is independently H, $-A_fH_{f+1}R^2_f$ or $-A_fH_fR^2_f-$ (where $R^2$ is H, halogen, aryl or substituted aryl), alkyl, alkylene, aralkyl, substituted aralkyl, halogen, aryl, arylene or substituted aryl, and when an instance of x=2, the two R groups may form a ring together with D; q is at least 1, but $q \geq 2$ when p=0; each of the q instances of a is independently at least 1; each of the q instances of b is independently an integer of from 1 to 2a; each of the q instances of m is an integer of from 1 to a; each of the q*m instances of x is independently 1 or 2; each instance of $R^1$ is independently H, $-A_fH_{f+1}R^2_f$, halogen, aryl or substituted aryl; each of the p instances of n is independently at least 1; each of the p*n instances of c is independently an integer of at least 1; each of the p*n instances of d is independently an integer of from c to 2c; each of the p*n instances of e is independently an integer of from 0 to c; and the sum of the p instances of $n*c \geq 4$ when q=1. In preferred embodiments, R is H, $-A_fH_{f+1}R^2_f$, alkyl, aryl or substituted aryl, and $R^1$ is independently H, halogen, aryl or substituted aryl. In general, the number of silicon and/or germanium atoms in the polysilane may be determined according to the number average molecular weight (Mn) of the polysilane. The compositions generally comprise the doped polysilane compound (particularly the doped polysilanes in which R=H, $C_1$-$C_6$ alkyl, phenyl or $-A_fH_{2f+1}$) and a solvent in which the doped polysilane is soluble.

In one aspect, the method of making a doped poly(aryl)silane generally includes the steps of mixing or combining a doped silane compound the formula $A_aH_{b+2}(DR_x)_m$ (optionally further including a silane compound of the formula $A_cH_{d+2}R^1_e$) with a catalyst of the formula $R^4_wR^5_yMX_z$ (or an immobilized derivative thereof) to form a doped poly(aryl)silane of the formula $H-[A_aH_b(DR_x)_m]_q-[(A_cH_dR^1_e)_n]_p-H$, then removing the metal M. In the doped silane and poly(aryl)silane, each instance of A is independently Si or Ge; D is B, P, As or Sb; each instance of R is independently H, $-A_fH_{f+1}R^2_f$ or $-A_fH_fR^2_f-$ (where $R^2$ is H, halogen, aryl or substituted aryl), alkyl, alkylene, aralkyl, substituted aralkyl, halogen, aryl, arylene or substituted aryl, and when an instance of x=2, the two R groups may form a ring together with D; q is at least 1, but $q \geq 2$ when p=0; each of the q instances of a is independently at least 1; each of the q instances of b is independently an integer of from 1 to 2a; each of the q instances of m is an integer of from 1 to a; each of the q*m instances of x is independently 1 or 2; each instance of $R^1$ is independently H, $-A_fH_{f+1}R^2_f$, halogen, aryl or substituted aryl; each of the p instances of n is independently at least 1; each of the p*n instances of c is independently an integer of at least 1; each of the p*n instances of d is independently an integer of from c to 2c; each of the p*n instances of e is independently an integer of from 0 to c; and the sum of the p instances of $n*c \geq 4$ when q=1. In the catalyst, M is a metal selected from the group consisting of Ti, Zr and Hf, x=1 or 2, y=1, 2 or 3, z=0, 1 or 2, $3 \leq (x+y+z) \leq 8$, each of the w instances of $R^4$ is independently a substituted or non-substituted cyclopentadienyl, indenyl, fluorenyl, siloxyl, germoxyl, hydrocarbyl, hydrocarbyloxy, hydrocarbylamino, or hydrocarbylsulfido ligand; each of the y instances of $R^5$ is independently a substituted or non-substituted hydrocarbyl, hydrocarbyloxy, hydrocarbylamino, hydrocarbylsulfido, silyl, (per)alkylsilyl, germyl, (per)alkylgermyl, hydride, phosphine, amine, sulfide, carbon monoxide, nitryl, or isonitryl ligand, and X is a halogen.

In another aspect, the method of making a doped polysilane includes the steps of halogenating a doped polyarylsilane made by the catalytic dehydrocoupling reaction step (a) described above, and reducing the doped halopolysilane with a metal hydride to form the doped polysilane.

The present invention is directed towards the synthesis of semiconductor inks via dehydrocoupling of doped (aryl)silanes and/or -germanes. Such synthesis allows for tuning of the ink properties (e.g., viscosity, boiling point, surface tension dopant level or concentration, etc.) and for deposition of doped silicon films or islands by spincoating, inkjetting, dropcasting, etc., with or without the use of UV irradiation. Thus, the invention further relates to a method of making or forming a doped or electrically active semiconductor film from the present ink composition, comprising the steps of: (A) spin-coating or printing the composition onto a substrate (optionally, with simultaneous or immediately subsequent UV irradiation); (B) heating the composition sufficiently to form a doped, amorphous, hydrogenated semiconductor; and (C) annealing and/or irradiating the doped, amorphous, hydrogenated semiconductor sufficiently to at least partially crystallize, reduce a hydrogen content of, and/or electrically activate the dopant in the doped, amorphous, hydrogenated semiconductor, and thus form the doped or electrically active semiconductor film.

These and other advantages of the present invention will become readily apparent from the detailed description of preferred embodiments below.

DETAILED DESCRIPTION OF THE PREFERRED EMBODIMENTS

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be readily apparent to one skilled in the art that the present invention may be practiced without these specific details. In other instances, well-known methods, procedures, components, and circuits have not been described in detail so as not to unnecessarily obscure aspects of the present invention.

For the sake of convenience and simplicity, the terms "$C_a$-$C_b$ alkyl," "$C_a$-$C_b$ alkoxy," etc., shall refer to both branched and unbranched moieties, to the extent the range from a to b covers 3 or more carbon atoms. Unless otherwise indicated, the terms "arene," "aryl," and "ar-" refer to both mono- and polycyclic aromatic species that may be unsubstituted or substituted with one or more conventional substituents, to the extent possible and/or applicable. The prefixes "(per)alkyl" and "(per)hydro" refer to a group having from one to all of its bonding sites substituted with alkyl groups or hydrogen atoms, respectively (e.g., "(per)alkylsilyl" refers to a silyl group of n atoms having from 1 to 2n+1 alkyl groups bound thereto). The terms "silane," "polysilane" and "(cyclo)silane" may be used interchangeably herein, and unless expressly indicated otherwise, these terms individually refer to a compound or mixture of compounds that consists essentially of (1) silicon and/or germanium and (2) hydrogen. The terms "arylsilane," "polyarylsilane" and "aryl(cyclo)silane" may be used interchangeably herein, and unless expressly indicated otherwise, these terms refer to a compound or mixture of compounds that contains or consists essentially of units having a silicon and/or germanium atom, a hydrogen atom bound thereto, and an aryl group bound thereto, where the aryl group may be substituted by a conventional hydrocarbon, silane or germane substituent. The term "(aryl)silane" refers to a silane, polysilane or cyclosilane that may or may not contain an aryl or substituted aryl group bound thereto. The terms "doped," "dopant" and grammatical variations thereof may be used interchangeably herein, and unless expressly indicated otherwise, these terms refer to a species, group or molecule containing a dopant atom such as B, P, As or Sb having a covalent bond to one or more conventional semiconductor element atoms (e.g., silicon and/or germanium). The prefix "(cyclo)-" generally refers to a compound or mixture of compounds that may contain a cyclic ring, and the prefix "cyclo-" or "c-" generally refers to a compound or mixture of compounds that contain one or more cyclic rings. For the sake of briefness, the terms "halo-," "halide" and grammatical derivations thereof may describe halogens as defined in the Periodic Table of Elements (F, Cl, Br, and I) and halogen-like species (e.g., that form stable monovalent anions) such as methanesulfonate (OMs), trifluoromethanesulfonate (OTf), toluenesulfonate (OTs), etc. Also, the terms "isolating" and "purifying" (and grammatical variations thereof) may be used interchangeably herein, but these terms are intended to have their art-recognized meanings, unless indicated otherwise.

The present invention concerns a doped polysilane, a "liquid silicon" ink composition containing the doped polysilane, methods for synthesizing the doped polysilane and for making the ink composition, and methods of using the doped polysilane and/or ink composition to make an electrically active semiconductor film. In general, the polysilane has the formula H-$[A_aH_b(DR_x)_m]_q$-$[(A_cH_dR^1_e)_n]_p$—, where each instance of A is independently Si or Ge; D is B, P, As or Sb; each instance of R is independently H, -$A_fH_{f+1}R^2_f$ or -$A_fH_fR^2_f$— (where $R^2$ is H, halogen, aryl or substituted aryl), alkyl, alkylene, aralkyl, substituted aralkyl, halogen, aryl, arylene or substituted aryl, and when an instance of x=2, the two R groups may form a ring together with D; q is at least 1, but q≧2 when p=0; each of the q instances of a is independently at least 1; each of the q instances of b is independently an integer of from 1 to 2a; each of the q instances of m is an integer of from 1 to a; each of the q*m instances of x is independently 1 or 2; each instance of $R^1$ is independently H, -$A_fH_{f+1}R^2_f$, halogen, aryl or substituted aryl; each of the p instances of n is independently at least 1; each of the p*n instances of c is independently an integer of at least 1; each of the p*n instances of d is independently an integer of from c to 2c; each of the p*n instances of e is independently an integer of from 0 to c; and the sum of the p instances of n*c≧4 when q=1. The composition generally comprises the polysilane compound (preferably where R and $R^1$ are H) and a solvent in which the polysilane is soluble.

Even further aspects of the invention concern methods of making a polysilane generally comprising the steps of (a) mixing or combining a doped silane compound the formula $A_aH_{b+2}(DR_x)_m$ (optionally further including a silane compound of the formula $A_cH_{d+2}R^1_e$) with a catalyst of the formula $R^4_wR^5_yMX_z$ (or an immobilized derivative thereof, or which can be synthesized in situ from corresponding precursors) to form a doped poly(aryl)silane of the formula H-$[A_aH_b(DR_x)_m]_q$-$[(A_cH_dR^1_e)_n]_p$—H, then removing the metal (i.e., in the catalyst) from the doped poly(aryl)silane. In the doped silane and poly(aryl)silane, each instance of A is independently Si or Ge; D is B, P, As or Sb; each instance of R is independently H, -$A_fH_{f+1}R^2_f$ or -$A_fH_fR^2_f$— (where $R^2$ is H, halogen, aryl or substituted aryl), alkyl, alkylene, aralkyl, substituted aralkyl, halogen, aryl, arylene or substituted aryl, and when an instance of x=2, the two R groups may form a ring together with D; q is at least 1, but q≧2 when p=0; each of the q instances of a is independently at least 1; each of the q instances of b is independently an integer of from 1 to 2a;

each of the q instances of m is an integer of from 1 to a; each of the q*m instances of x is independently 1 or 2; each instance of $R^1$ is independently H, $-A_fH_{f+1}R^2_f$, halogen, aryl or substituted aryl; each of the p instances of n is independently at least 1; each of the p*n instances of c is independently an integer of at least 1; each of the p*n instances of d is independently an integer of from c to 2c; each of the p*n instances of e is independently an integer of from 0 to c; and the sum of the p instances of n*c≧4 when q=1. In the catalyst, M is a metal selected from the group consisting of Ti, Zr and Hf, w=1 or 2, y=1, 2 or 3, z=0, 1 or 2, 3≦(x+y+z)≦8, each of the w instances of $R^4$ is independently a substituted or non-substituted cyclopentadienyl, indenyl, fluorenyl, siloxyl, germoxyl, hydrocarbyl, hydrocarbyloxy, hydrocarbylamino, or hydrocarbylsulfido ligand; each of the y instances of $R^5$ is independently a substituted or non-substituted hydrocarbyl, hydrocarbyloxy, hydrocarbylamino, hydrocarbylsulfido, silyl, (per)alkylsilyl, germyl, (per)alkylgermyl, hydride, phosphine, amine, sulfide, carbon monoxide, nitryl, or isonitryl ligand, and X is a halogen.

Alternatively, the method may first form a doped polyarylsilane by mixing or combining the doped silane compound of the formula $A_aH_{b+2}(DR_x)_m$ and the silane compound of the formula $A_cH_{d+2}R^1_e$ (in which at least one instance of $R^1$ is aryl) with the catalyst in accordance with step (a), then perform the steps of (b') reacting the doped polyarylsilane with (i) a halogen source and (optionally) a Lewis acid, or (ii) trifluoromethanesulfonic acid (HOTf), to form a doped halopolysilane; and (c') reducing the doped halopolysilane with a metal hydride to form a doped polysilane of the formula $H-[A_aH_b(DR_x)_m]_q-[(A_{c+g}H_{d+h})_n]_p-H$, where g is the number of A atoms in the instances of $R^1$ where $R^1$ is $-A_fH_{f+1}R^2_f$ and h is a number of from e to [2(c+g)-h].

The invention further relates to a method of making or forming a doped or electrically active semiconductor film from the present ink composition, comprising the steps of: (A) spin-coating or printing the composition onto a substrate (optionally, with simultaneous or immediately subsequent UV irradiation); (B) heating the composition sufficiently to form a doped, amorphous, hydrogenated semiconductor; and (C) annealing and/or irradiating the doped, amorphous, hydrogenated semiconductor sufficiently to at least partially crystallize, reduce a hydrogen content of and/or electrically activate the dopant in the doped, amorphous, hydrogenated semiconductor, and thus form the doped or electrically active semiconductor film.

Doped poly- and oligo-hydrosilane and -hydrogermane semiconductor inks can be synthesized by dehydrocoupling of silyl- and/or germylphosphines (e.g., $PH_jR_{3-j}$, where j is 0, 1 or 2, at least one R is $-A_fH_{f+1}R^2_f$ or at least two R groups together are $-A_fH_fR^2_f-$) or silyl- and/or germylboranes (e.g., $BH_jR_{3-j}$, where j is 0, 1 or 2, at least one R is $-A_fH_{f+1}R^2_f$ or at least two R groups together are $-A_fH_fR^2_f-$), optionally with perhydrosilanes and perhydrogermanes (linear, branched, cyclo-, caged, poly-, or oligosilanes and/or -germanes), or by dehydrocoupling of arylhydrosilanes and arylhydrogermanes with such silyl- and/or germylphosphines or silyl- and/or germylboranes, followed by halogenative cleavage of the aryl groups and metal hydride reduction to yield doped perhydrosilanes and perhydrogermanes. The dopant level in the ink compositions can be controlled by the ratio of dopant compound (e.g., the silyl- and/or germylphosphine or -borane) to perhydro- or arylhydrosilane or -germane in the dehydrocoupling reaction. The inks are used for production of amorphous or polycrystalline silicon, germanium, or silicon-germanium films by spincoating or inkjet printing, followed by curing at 400-500° C. and (optionally) laser-, heat-, or metal-induced crystallization and/or dopant activation. Highly doped films may be used to make contact layers in MOS capacitors, TFTs, diodes, etc. Lightly doped films may be used as semiconductor films in MOS capacitors, TFTs, diodes, etc.

The invention, in its various aspects, will be explained in greater detail below with regard to exemplary embodiments.

An Exemplary Doped Polysilane

In one aspect, the present invention relates to a doped polysilanes generally have the formula $H-[A_aH_b(DR_x)_m]_q-[(A_cH_dR^1_e)_n]_p-H$, where each instance of A is independently Si or Ge; D is B, P, As or Sb; each instance of R is independently H, $-A_fH_{f+1}R^2_f$ or $-A_fH_fR^2_f-$ (where $R^2$ is H, halogen, aryl or substituted aryl), alkyl, alkylene, aralkyl, substituted aralkyl, halogen, aryl, arylene or substituted aryl, and when an instance of x=2, the two R groups may form a ring together with D; q is at least 1, but q≧2 when p=0; each of the q instances of a is independently at least 1; each of the q instances of b is independently an integer of from 1 to 2a; each of the q instances of m is an integer of from 1 to a; each of the q*m instances of x is independently 1 or 2; each instance of $R^1$ is independently H, $-A_fH_{f+1}R^2_f$, halogen, aryl or substituted aryl; each of the p instances of n is independently at least 1; each of the p*n instances of c is independently an integer of at least 1; each of the p*n instances of d is independently an integer of from c to 2c; each of the p*n instances of e is independently an integer of from 0 to c; and the sum of the p instances of n*c≧4 when q=1. In preferred embodiments, R is H, $-A_fH_{f+1}R^2_f$, alkyl, aryl or substituted aryl, and $R^1$ is independently H, halogen, aryl or substituted aryl. In general, the number of silicon and/or germanium atoms in the polysilane may be determined according to the number average molecular weight (Mn) of the polysilane. Doped polysilanes having both cyclic blocks and linear/branched chains are contemplated. Thus, "p" and "q" may represent one or more blocks of substantially linear, branched or cyclic chains of silicon atoms in the polysilane. Thus, in general, the doped polysilane may comprise a doped homopolymer of repeating $-(-A_aH_{2a-m}(DR_x)_m-)-$, $-(-A_aH_{2a}(DR)_m-)-$, $-(-c-[A_aH_{2a-2}(DR)_m]-)-$ or $-(c-[A_aH_{2a-2-m}](DR_2)_m-)-$ units, or a copolymer comprising one or more doped homopolymer blocks with one or more undoped blocks of repeating $-(-AHR—)—$, $-(-A_kH_{2k}—)—$ and/or $-(c-A_mH_{2m-2})—$ units, each of which may include one or more such units in a given block.

In various preferred embodiments, D is B or P, and R is H, $-A_fH_{f+1}R^2_f$ (where f is an integer≦6), alkyl, halogen, or aryl. More preferably, R may be H, $-A_fH_{2f+1}$ where f is an integer≦4, $C_1-C_6$ alkyl, phenyl or tolyl. Even more preferably, R is $C_1-C_4$ alkyl (e.g., t-butyl).

In other embodiments of the present doped polysilane, a is at least 2 (preferably at least 3), b is from a to 2a, and m is 1 or 2. Thus, a may be an integer of from 2 to 6, and b may be (2a-2-m) when the "$A_aH_b$" moiety is cyclic and "$DR_x$" is exocyclic, (2a -m) when the "$A_aH_b$" moiety is linear or branched and "$DR_x$" is not in the polymer chain or backbone (e.g., "$DR_x$" is a substituent), (2a-2) when the "$A_aH_b$" moiety is cyclic and "$DR_x$" is endocyclic, or 2a when the "$A_aH_b$" moiety is linear or branched and "DR" is in the polymer chain or backbone (in this latter case, x=1). Thus, the doped polysilane may have an average number of A atoms of at least 10 (preferably at least 12, 15 or any other number greater than 10) according to or as calculated from a number average molecular weight Mn of the doped polysilane. In some examples, the number of A atoms (e.g., Si atoms in the chain or otherwise covalently bound thereto) may reach 50 or more.

A first exemplary doped polysilane has the formula $H-[A_aH_b(DR_x)_m]_q-H$ (i.e., where p=0), where each instance of A is independently Si or Ge; each instance of R is independently H, halogen, alkyl, aryl, substituted aryl, or $-A_fH_{f+1}R^2_f$ (where $R^2$ is H, aryl or substituted aryl); and $(q*[a+x*f]) \geq 10$. In general, the polysilane has a linear structure (i.e., where the polymer chain consists essentially of A atoms or a combination of A and D atoms), but branched analogs (e.g., where R is $-A_bH_{b+1}R^2_b$) are possible. Generally, such branched analogs will be present in a mixture with one or more linear polysilanes. In general, the sum of the q instances of (a plus the x instances of f), or the q instances of (a plus the x instances of f) plus the p instances of n*c represent an average number of silicon and/or germanium atoms in the product mixture, and in most cases, that average number is less than or equal to 50 (preferably less than or equal to 25 or 30). For example, when the polysilane is linear, the average number of A atoms (or A and D atoms) $\leq 50$. However, under typical conditions and/or using certain known catalysts and/or monomers, the average number of A atoms (or A and D atoms) is more typically $\leq 25$ or 30.

In certain embodiments of the present doped polysilane, p and q are at least 1, $n*p \geq 4$ (e.g., n*p has an average value for a given dehydrocoupling reaction product mixture of at least 10), $R^1$ is phenyl, tolyl, Cl or H (preferably H), and/or A is Si. However, in other embodiments, at least one A is Ge. In such an embodiment, the doped polygermasilane is essentially a random and/or statistical mixture of doped polysilanes, polygermanes and polygermasilanes containing a proportion or ratio of germanium-to-silicon atoms that substantially corresponds to the proportion or ratio of the germanium atoms to silicon atoms in the mixture of monomeric starting materials, as may be more fully explained herein.

The structure and nature of the present poly(aryl)silanes and poly(halo)silanes may be better understood with reference to some exemplary methods for their synthesis.

An Exemplary Method of Making Doped Poly(aryl)silanes

In general, doped oligo- and polyhydrosilane and -hydrogermane compounds for semiconductor inks can be synthesized by dehydrocoupling of hydrosilanes and/or hydrogermanes containing dopant atoms (e.g., where and A=Si or Ge), to form linear, branched, cyclic, and/or heteropolysilanes and/or heteropolygermanes, and removing the catalyst metal from the doped poly(aryl)silane. Such metal removal may comprise contacting the doped poly(aryl)silane with an adsorbent sufficiently to remove the metal, and optionally, washing the doped poly(aryl)silane with an aqueous washing composition. This aspect of the invention focuses on dehydrocoupling of doped hydrosilanes and/or doped hydrogermanes (e.g., compounds as small as $D(AH_3)_3$, where D is a conventional semiconductor dopant atom and A=Si or Ge).

Dehydrocoupling of arylhydrosilanes using titanium (Ti), zirconium (Zr), hafnium (Hf), neodymium (Nd) and uranium (U) catalysts is known (see, e.g., T. D. Tilley, *Acc. Chem. Res.* 1993, vol. 26, pp. 22-29; V. K. Dioumaev and J. F. Harrod, *J. Organomet. Chem.* vol. 521 [1996], pp. 133-143; and Q. Wang and J. Y. Carey, *Can. J. Chem.* vol. 78 [2000], pp. 1434-1440). In part, the present invention relates to use of this approach to synthesize novel doped polyarylhydrosilanes, -germanes and/or -silagermanes, and to an improved method for synthesizing doped polyarylhydrosilanes, -germanes and/or -silagermanes that eliminates the metal catalyst to a significantly greater degree than alternative approaches, thereby significantly improving the stability of subsequently-produced polyhydrosilanes, -germanes and/or -silagermanes.

Thus, in one aspect, the present invention relates to a method of making a doped poly(aryl)silane, generally including the steps of mixing or combining a doped silane compound of the formula $A_aH_{b+2}(DR_x)_m$ (optionally further including a silane compound of the formula $A_cH_{d+2}R^1_e$) with a catalyst of the formula $R^4_wR^5_yMX_z$ (or an immobilized derivative thereof, or which can be synthesized in situ from corresponding precursors) to form a doped poly(aryl)silane of the formula $H-[A_aH_b(DR_x)_m]_q-[(A_cH_dR^1_e)_n]_p-H$, then removing the metal (i.e., in the catalyst) from the doped poly(aryl)silane. Doped silanes of the formula $A_aH_{b+2}(DR_x)_m$ (and/or examples thereof) are or may be generally disclosed in one or more of U.S. patent application Ser. Nos. 10/949,013, 10/950,373 and 10/956,714, respectively filed on Sep. 24, 2004, Sep. 24, 2004, and Oct. 1, 2004, the relevant portions of which are incorporated herein by reference.

In the doped silane and poly(aryl)silane, each instance of A is independently Si or Ge; D is B, P, As or Sb; each instance of R is independently H, $-A_fH_{f+1}R^2_f$ or $-A_fH_fR^2_f-$ (where $R^2$ is H, halogen, aryl or substituted aryl), alkyl, alkylene, aralkyl, substituted aralkyl, halogen, aryl, arylene or substituted aryl, and when an instance of x=2, the two R groups may form a ring together with D; q is at least 1, but $q \geq 2$ when p=0; each of the q instances of a is independently at least 1; each of the q instances of b is independently an integer of from 1 to 2a; each of the q instances of m is an integer of from 1 to a; each of the q*m instances of x is independently 1 or 2; each instance of $R^1$ is independently H, $-A_fH_{f+1}R^2_f$, halogen, aryl or substituted aryl; each of the p instances of n is independently at least 1; each of the p*n instances of c is independently an integer of at least 1; each of the p*n instances of d is independently an integer of from c to 2c; each of the p*n instances of e is independently an integer of from 0 to c; and the sum of the p instances of $n*c \geq 4$ when q=1. In the catalyst, M is a metal selected from the group consisting of Ti, Zr and Hf, w=1 or 2, y=1, 2 or 3, z=0, 1 or 2, $3 \leq (x+y+z) \leq 8$, each of the w instances of $R^4$ is independently a substituted or non-substituted cyclopentadienyl, indenyl, fluorenyl, siloxyl, germoxyl, hydrocarbyl, hydrocarbyloxy, hydrocarbylamino, or hydrocarbylsulfido ligand; each of the y instances of $R^5$ is independently a substituted or non-substituted hydrocarbyl, hydrocarbyloxy, hydrocarbylamino, hydrocarbylsulfido, silyl, (per)alkylsilyl, germyl, (per)alkylgermyl, hydride, phosphine, amine, sulfide, carbon monoxide, nitryl, or isonitryl ligand, and X is a halogen.

Preferably, the metal M in the dehydrocoupling catalyst is Zr or Hf. These metals tend to provide a sufficient balance between dehydrocoupling rate or activity, doped poly(aryl)silane molecular weight and content of (doped) cyclosilane by-products (e.g., Hf generally produces a higher proportion of linear polysilane products than Zr). In various embodiments, w is 2 and $R^4$ is cyclopentadienyl (Cp), permethylcyclopentadienyl (Cp*), indenyl or fluorenyl (Fl). Having at least one bulky or substituted cyclopentadienyl ligand (e.g., Cp*, indenyl or fluorenyl) tends to promote dehydrocoupling by reducing a tendency of the catalyst to dimerize, but the catalyst is not at all required to have such a ligand. Also, in various embodiments, y is 2 and $R^5$ in the dehydrocoupling catalyst is H, $C_1$-$C_6$ alkyl, $C_6$-$C_{12}$ aryl, $SiR^2_3$, or $Si(SiR^2_3)_3$, where $R^2$ is H or $C_1$-$C_4$ alkyl. Such ligands are believed to promote metathesis of Si—H or Ge—H bonds in the starting silane compound.

In general, to remove the metal from the doped poly(aryl)silane, a solution of the doped poly(aryl)silane in a suitable organic solvent (typically the washed doped poly[aryl]silane) is contacted with the adsorbent for a length of time sufficient for the adsorbent to adsorb the metal from the catalyst. The adsorbent generally comprises a chromatography gel or finely divided silicon and/or aluminum oxide that is substantially unreactive with the polyarylsilane. Examples of suitable adsorbents include silica gel, alumina, FLUORISIL, and CELITE. In one embodiment, such contacting comprises passing the doped poly(aryl)silane through a column packed with the adsorbent. Alternatively, a solution of the doped poly(aryl)silane may be mixed with the adsorbent for a length of time sufficient for the adsorbent to adsorb the metal/catalyst from the solution. The adsorbent is generally removed from the adsorption mixture by conventional filtration. Alternatively, the metal may be removed by adding an inactivating ligand (somewhat surprisingly, such as a trialkyl- or triarylphosphine), then removing the inactivated catalyst by a conventional process (e.g., precipitating one of the doped polysilane and the inactivated catalyst with an appropriate solvent, filtering and optionally removing the solvent; by crystallization or recrystallization, by vacuum distillation of the doped polysilane, etc.)

Generally, some doped polysilanes may have A-D bonds (e.g., Si—P bonds) that may be sensitive to hydrolysis. As a result, washing the doped poly(aryl)silane is optional, and should be employed only when the doped poly(aryl)silane does not contain easily hydrolyzable A-D bonds. The washing composition may comprise deionized water or dilute aqueous acid. For example, the aqueous acids suitable for use in the present method generally include the mineral acids and their equivalents, such as hydrochloric acid, hydrobromic acid, trifluoroacetic acid, and trifluoromethanesulfonic acid. Preferably, the aqueous acid comprises hydrochloric acid. The dilution factor for the washing composition may be from 1:1 to 1:1000 (concentrated mineral acid to water), generally by volume. For example, the dilute aqueous acid may comprise from 0.1 to 10 vol. % (e.g., from 1 to 5 vol. %) of conc. HCl in deionized water. In one implementation, doped poly (aryl)silane washing comprises washing the doped poly(aryl) silane one or more times with dilute aqueous acid, followed by washing the acid-washed doped poly(aryl)silane one or more times with water.

Figure 1:
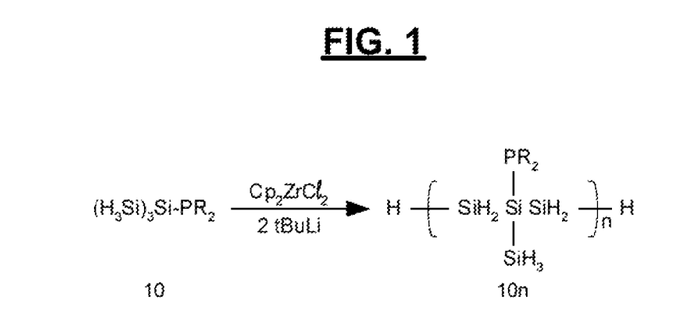
FIG. 1 is a diagram showing an approach for the synthesis of doped polysilanes from doped silanes by catalytic dehydrocoupling.

Referring now to FIG. 1, in a first exemplary embodiment of the present method, a linear or branched doped silane compound of the formula $A_aH_{2a+1}DR_2$ (e.g., $(H_3Si)_3Si—PR_2$ 10) may be catalytically dehydrocoupled (or dehydrogenatively metathesized) using a Group IVB transition metal catalyst, such as $Cp_2Zr(t-Bu)_2$, generated in situ from $Cp_2ZrCl_2$ and about 2 mole equivalents of t-butyl lithium, to form poly($H_2Si$—Si($SiH_3$)($PR_2$)—$SiH_2$) 10n. Thus, in preferred implementations of this embodiment, A is Si, a is 4 and/or b is (2a−m). However, R may be H, alkyl, aryl, or $-A_fH_{2f+1}$, and both R groups taken together may be alkylene (e.g., —$PR_2$ is -c-P($CH_2$)$_4$), arylene (e.g., —$PR_2$ is -c-P($\alpha,\alpha'$-diphenylene)), or silylene (e.g., —$PR_2$ is -c-P($SiH_2$)$_4$, -c-P($SiPh_2$)$_4$, or -c-P($SiMe_2$)$_4$). Preferably, R is H, phenyl, $-A_fH_{2f+1}$ (where f is an integer from 1 to 4), or $C_1$-$C_6$ alkyl (e.g., isopropyl or t-butyl).

Where R is $-A_fH_{2f+1}$, it is likely that a significant proportion of cyclic and/or caged products are formed. For example, dehydrocoupling of ($H_3Si$)$_3Si$—$PR_2$ 10 may form a relatively small proportion of cyclic dimer [($H_2Si$)$_2$(Si—$PR_2$)]$_2$ (not shown). Although the doped polysilanes may be separated and/or isolated from the cyclic dimer or other relatively low molecular weight compounds, the relatively low molecular weight cyclic compounds generally do not affect subsequent steps in the synthesis of doped polysilanes.

The dehydrocoupling reaction evolves hydrogen gas, and thus, tends to be irreversible if the hydrogen gas is removed from the dehydrocoupling reaction vessel. Generally, the polymerization/dehydrocoupling reaction time is from a few hours (e.g., 3, 4, 6 or more hours) to a few days (e.g., 3, 4 or 5 days). The reaction mixture may be formed by dropwise addition of the monomer to a solution of the catalyst, or by mixing the catalyst directly with the monomer. In fact, neat solutions of doped silane/germane monomer and catalyst tend to provide higher molecular weights (e.g., number average molecular weights, or Mn) of doped poly(aryl)silanes. The reaction temperature may also be kept relatively low (e.g., from about 0 to about 30° C.), generally to promote higher doped poly(aryl)silane molecular weights and/or to reduce the amount of relatively low molecular weight and/or cyclic silane compounds. However, in some cases (e.g., when a sterically crowded catalyst and/or monomer is/are used), a higher temperature may be advantageous for increasing the reaction rate.

As shown in FIG. 1, the dehydrocoupling catalyst $Cp_2Zr(t-Bu)_2$ may be generated in situ from a zirconocene halide (e.g., $Cp_2ZrCl_2$) and an alkyl, aryl or peralkylsilyl metal reagent (e.g., an alkyllithium reagent such as t-butyllithium or PhMgBr, which can also be generated in situ in accordance with known techniques). Thus, dehydrogenative metathesis may be conducted using a diaryl-, bis(peralkylsilyl)-, aryl (peralkylsilyl)-, dialkyl- or alkyl(peralkylsilyl) metallocene catalyst such as $Cp_2ZrPh_2$. Further, the metal M, or one or more of the w instances of $R^4$, y instances of $R^5$ or z instances of X, can be independently bound to a silica, alumina, or polymer surface rendering the catalyst heterogeneous. The polymer is typically a hydrocarbon polymer, such as polyethylene, polypropylene, polystyrene, a polyethylene-polypropylene or polyethylene-polystyrene copolymer, etc.

Alternative catalysts can include any conventional dehydrocoupling catalyst, especially those containing a Group 4 element. For example, an Hf analog of the Zr catalyst in FIG. 1 will generally reduce the amount of cyclic silane compounds produced. Also, as mentioned above, metallocene catalysts containing a relatively bulky ligand, such as CpCp*Zr(SiMe$_3$)Ph, may provide higher molecular weight polysilanes (e.g., having a Mn as high as 5000 Daltons [i.e., 25-45 Si atoms]). By contrast, the Mn of a polyphenylsilane produced from PhSiH$_3$ using Cp$_2$ZrPh$_2$ is generally around 1200 Daltons (i.e., in a polymer of the formula H—(SiH$_2$)$_n$—H, n≈10-12). Use of a sterically crowded catalyst like CpCp*Zr(SiMe$_3$)Ph is expected to produce a higher viscosity doped polysilane ink composition.

Typical conditions for dehydrocoupling reaction include a temperature of about ambient or room temperature, a pressure of about atmospheric pressure (or about 1 atm) of inert gas under dynamic conditions (e.g., in a reaction vessel having somewhat free gas out-flow, such as a gas bubbler, generally to allow escape of evolved hydrogen gas). The typical catalyst loading may be >1 mol % (e.g., from 1 to 10 mol %, 2 to 5 mol %, or any range of values therein, relative to the molar quantity of monomer) for dehydrocoupling of doped silanes and doped germanes.

The adsorbing step in the present method is generally used to remove the metal of the catalyst (e.g., Zr in FIG. 1) from the doped polysilane 10n. Conventional chromatography methods using gels, such as FLORISIL, and other gels like silica, alumina, and CELITE are generally suitable. Alternatively, the gel is added to a doped polysilane 10n solution and stirred (generally for a length of time sufficient to remove some or substantially all of the metal from the solution), then the gel is generally removed by filtration. Contacting a chromatography gel with a solution of the doped polysilane 10n can be substituted by simply passing the solution of doped polysilane 10n through a thick pad of the gel.

The solvents used in the procedure are not limited. Cyclohexane, toluene, and diethyl ether are generally preferred, although any solvent or mixture of solvents with relatively low boiling points (e.g., ≦100° C., ≦80° C., or ≦60° C.), compatible with doped poly(aryl)silanes, are suitable.

Figure 2:
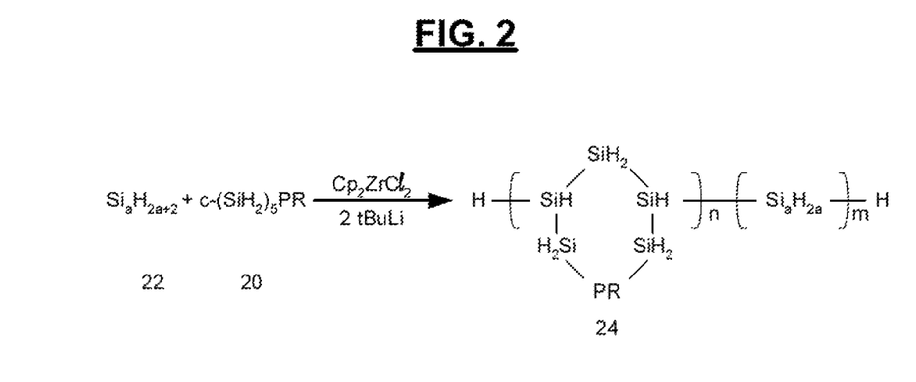
FIG. 2 is a diagram showing an approach for the synthesis of doped polysilanes from doped cyclosilanes by catalytic dehydrocoupling, in which units of doped and undoped silanes are identified by q and np, respectively, in the general formula.

FIG. 2 shows a second exemplary scheme illustrating dehydrocoupling of doped cyclosilane monomer c-(SiH$_2$)$_5$P—C(CH$_3$)$_3$ 20 (i.e., where R=t-butyl) and linear or branched (undoped) silane A$_a$H$_{2a+2}$ 22 using the catalyst of FIG. 1 to form a copolymer 24. In this copolymer, (np+q)≧3, 5, or more. In the doped polysilane product 24, n and m may represent the sum of two or more blocks in the polymer (e.g., n=n$_1$+n$_2$+ . . . +n$_x$), and may generally represent a random and/or statistical mixture corresponding to the molar ratio of c-(SiH$_2$)$_5$P—C(CH$_3$)$_3$ 20 to undoped silane A$_a$H$_{2a+2}$ 22 in the dehydrocoupling reaction mixture. Thus, m may be anywhere from 1 to (n−1), but more typically, the molar ratio of undoped silane (e.g., A$_a$H$_{2a+2}$ 22) to doped silane monomer (e.g., c-(SiH$_2$)$_5$P—C(CH$_3$)$_3$ 20) is anywhere from 1:1 to 20:1, and thus, n will typically be an integer of from 1 to m. Furthermore, the resulting reaction mixtures may contain both heterocoupled polymers of doped (cyclic) silanes and undoped (linear/branched) silanes, and homocoupled polymers of doped or undoped silanes.

Figure 5:
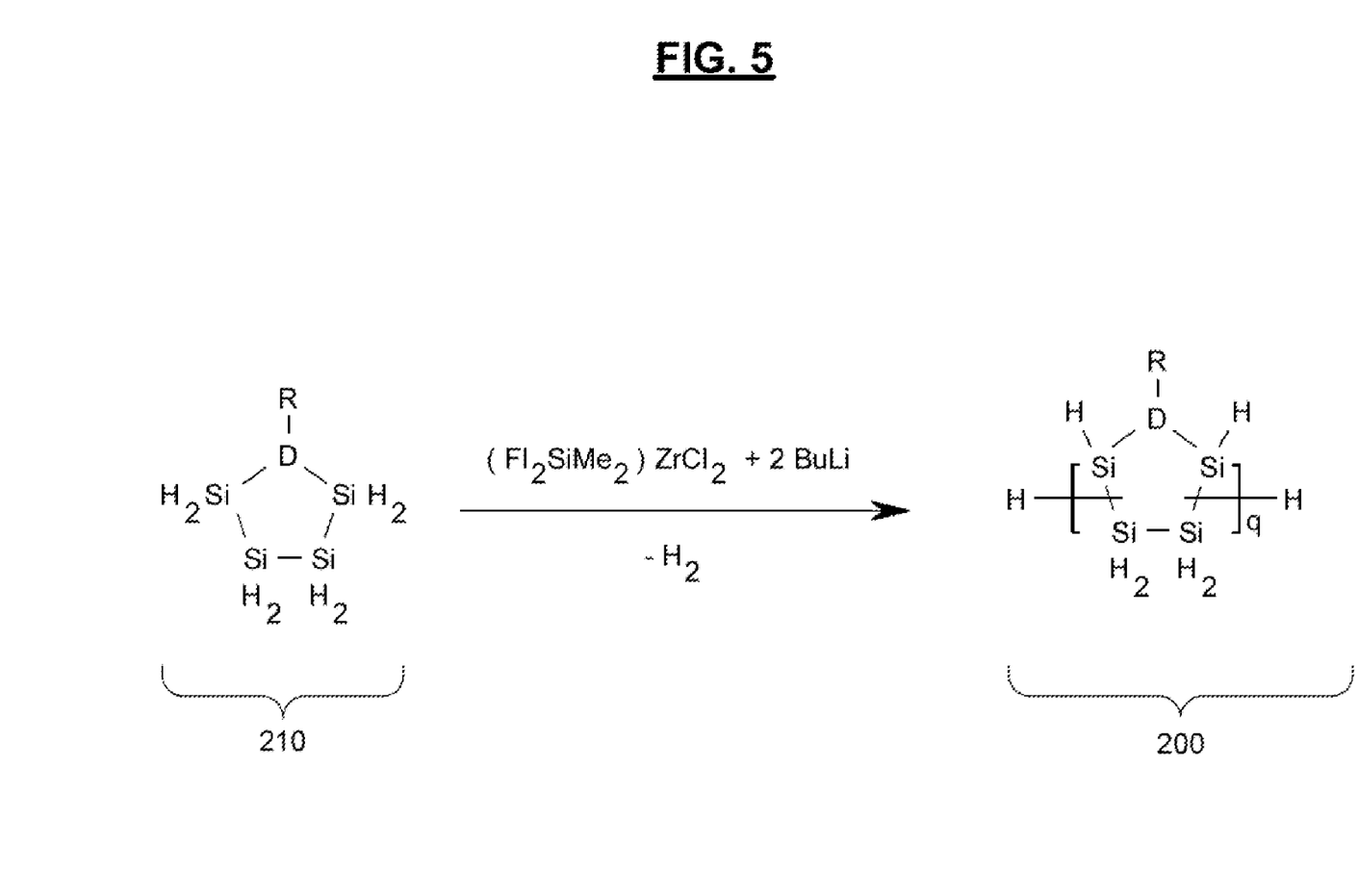
FIG. 5 is a diagram showing an approach for the synthesis of doped polycyclosilanes from a doped cyclosilane by catalytic dehydrocoupling.

Referring now to FIG. 5, in a further exemplary embodiment of the present method, a doped cyclosilane compound of the formula c-(A$_a$H$_{2a}$)DR (e.g., c-(SiH$_2$)$_4$DR 210) may be catalytically dehydrocoupled (or dehydrogenatively methathesized) using a Group IVB transition metal catalyst, such as (Me$_2$SiFl$_2$)ZrBu$_2$, generated in situ from (Me$_2$SiFl$_2$)ZrCl$_2$ and about 2 mole equivalents of butyllithium, to form poly(c-(Si$_4$H$_6$DR) 200. Doped silanes of the formula c-(A$_a$H$_{2a}$)DR (and/or examples thereof) are or may be disclosed in U.S. patent application Ser. Nos. 10/950,373 and/or 10/956,714, respectively filed on Sep. 24, 2004, Sep. 24, 2004, and Oct. 1, 2004, the relevant portions of which are incorporated herein by reference. Thus, in such an approach, a may be 4 or 5, and b may be (2a−2). In preferred implementations of this embodiment, D is B or P, and R may be phenyl, -A$_f$H$_{2f+1}$ (where f is an integer from 1 to 4), or C$_1$-C$_6$ alkyl (e.g., t-butyl).

In the scheme of FIG. 5, where R is -A$_f$H$_{2f+1}$, a proportion of cyclic and/or caged products may be formed. For example, dehydrocoupling of c-(H$_2$Si)$_4$P—SiH$_3$ 210 (i.e., where R=SiH$_3$) may form a relatively small proportion of cyclic dimer c-(H$_2$Si)$_4$P—(SiH$_2$)$_2$-c-P(SiH$_2$)$_4$ (not shown). Although the doped polysilanes may be separated and/or isolated from the cyclic dimer or other relatively low molecular weight compounds, the relatively low molecular weight cyclic compounds generally do not affect subsequent steps in the synthesis of doped polysilanes.

Another approach for making doped polysilanes by dehydrocoupling (but not necessarily catalytically) involves direct coupling of a linear, branched or cyclic silane with a primary organophosphine or organoborane dopant:

In this case, the starting silane should be a poly(aryl)silane or poly(cyclo)silane (e.g., containing at least 10 A atoms), but such a poly(aryl)silane may comprise the reaction mixture from the catalytic dehydrocoupling of an arylsilane monomer such as PhSiH$_3$, as disclosed in U.S. application Ser. No. 11/246,014, (the relevant portions of which are incorporated herein by reference). When R is a relatively labile group (such as t-butyl), the carbon and/or hydrogen content in an annealed and/or crystallized semiconductor film formed from the doped polysilane immediately above should be relatively small and/or insignificant in terms of the desired electrical properties of the film.

An Exemplary Method of Making Doped Polysilanes

Cleavage of aryl groups bound to Si or Ge, and reduction of silicon and/or germanium halides and pseudo-halides are generally disclosed in, e.g., U.S. patent application Ser. Nos. 10/789,317, 10/949,013, 10/950,373 and 10/956,714, respectively filed on Feb. 27, 2004, Sep. 24, 2004, Sep. 24, 2004, and Oct. 1, 2004, the relevant portions of which are incorporated herein by reference. Typically, and as shown in FIGS. 3-4 and 6-7, this cleavage reaction is conducted with HCl and AlCl$_3$. However, as is also known, a conventional chlorination-based cleavage reaction can be substituted with HBr to obtain a polybromosilane, or with TfOH to obtain a poly(trifluoromethanesulfonyl)silane. Thus, the present invention also relates to the combination of (1) catalytic dehydrocoupling as described above and (2) the cleavage and reduction processes described herein, to synthesize doped polyhydrosilanes, -germanes and/or -silagermanes.

Thus, in another aspect, the present invention concerns a method of making a doped polysilane, comprising the steps of (a) combining or mixing a doped silane of the formula A$_a$H$_{b+2}$(DR$_x$)$_m$ and an arylsilane compound of the formula A$_c$H$_{d+2}$R$^1_e$ with a catalyst of the formula R$^4_w$R$^5_y$MX$_z$ (or an immobilized derivative thereof, or which may be synthesized in situ from corresponding precursors) to form a doped polyarylsilane of the formula H-[A$_a$H$_b$(DR$_x$)$_m$]$_q$-[(A$_c$H$_d$R$^1_e$)$_n$]$_p$—H, (b) reacting the doped polyarylsilane with (i) d a halogen source and (optionally) a Lewis acid or (ii) trifluoromethanesulfonic acid (HOTf), to form a doped halopolysilane; and (c) reducing the doped halopolysilane with a metal hydride to form a doped polysilane of the formula H-[A$_a$H$_b$(DR$_x$)$_m$]$_q$-[(A$_{c+g}$H$_{d+h}$)$_n$]$_p$—H, where g is the number of A atoms in the instances of R$^1$ where R$^1$ is -A$_f$H$_{f+1}$R$^2_f$, and h is a number of from e to (e+2 g). In the doped silane and the doped polysilane, each instance of A is independently Si or Ge; D is B, P, As or Sb; each instance of R is independently H, -A$_f$H$_{f+1}$R$^2_f$ or -A$_f$H$_f$R$^2_f$— (where R$^2$ is H, halogen, aryl or substituted aryl), alkyl, alkylene, aralkyl, substituted aralkyl, halogen, aryl, arylene or substituted aryl, and when an instance of x=2, the two R groups may form a ring together with D; q and p are each at least 1; each of the q instances of a is independently at least 1; each of the q instances of b is independently an integer of from 1 to 2a; each of the q instances of m is an integer of from 1 to a; each of the q*m instances of x is independently 1 or 2; each instance of R$^1$ is independently H, -A$_f$H$_{f+1}$R$^2_f$, aryl or substituted aryl, but at least 1 instance of R$^1$ is aryl or substituted aryl; each of the p instances of n is independently at least 1; each of the p*n instances of c is independently an integer of at least 1; each of the p*n instances of d is independently an integer of from (c−1) to (2c−1); and each of the p*n instances of e is independently an integer of from 1 to c. In the catalyst, M is a metal selected from the group consisting of Ti, Zr and Hf, w=1 or 2, y=1, 2 or 3, z=0, 1 or 2, 3≦(x+y+z)≦8, each of the w instances of R$^4$ is independently a substituted or non-substituted cyclopentadienyl, indenyl, fluorenyl, siloxyl, germoxyl, hydrocarbyl, hydrocarbyloxy, hydrocarbylamino, or hydrocarbylsulfido ligand; each of the y instances of R$^5$ is independently a substituted or non-substituted hydrocarbyl, hydrocarbyloxy, hydrocarbylamino, hydrocarbylsulfido, silyl, germyl, hydride, phosphine, amine, sulfide, carbon monoxide, nitryl, or isonitryl ligand, and X is a halogen.

Generally, the method comprises combining a doped silane of the formula $A_cH_{b+2}(DR_x)_m$ and an arylsilane compound of the formula $A_cH_{d+2}R^1{}_e$ (e.g., $AH_3R^1$) with a catalyst of the formula $R^4{}_wR^5{}_yMX_z$ to form a doped polyarylsilane of the formula $H$-$[A_aH_b(DR_x)_m]_q$-$[(A_cH_dR^1{}_e)_n]_p$-$H$. Doped silanes of the formula $A_aH_{b+2}(DR_x)_m$ are or may be disclosed in one or more of U.S. patent application Ser. Nos. 10/949, 013, 10/950,373 and 10/956,714, respectively filed on Sep. 24, 2004, Sep. 24, 2004, and Oct. 1, 2004, the relevant portions of which are incorporated herein by reference. Also, as described in copending U.S. application Ser. No. 11/246,014, (the relevant portions of which are incorporated herein by reference), arylsilane compounds of the formula $A_kH_gR^{1'}{}_h$ (particularly where k is an integer of at least 2, g=[k+2], and h=k) are likely to be present in a dehydrocoupling reaction mixture containing an arylsilane compound of the formula $A_cH_{d+2}R^1{}_e$ (particularly homocoupled oligomers or polymers of the silane of the formula $AH_3R^1$). As a result, the present method contemplates use of linear, branched or cyclic arylhydrosilanes of the formula $A_cH_{d+2}R^{1'}{}_e$ for making doped polyarylsilanes.

Also, in certain embodiments, the method comprises reacting the polyarylsilane with the halogen source and the Lewis acid, wherein the Lewis acid comprises a compound of the formula $M^3{}_vX^2{}_u$, where $M^3$ comprises a member selected from the group consisting of transition metals and Group IIIA elements; v is 1 or 2; $X^2$ comprises a halogen; and u is any integer up to the number of ligand binding sites available on the v instances of $M^3$. In a preferred embodiment, $M^3$ comprises Al, and $X^2$ is Cl or Br (e.g., Cl, as shown in FIGS. 3-4 and 6-7).

In further embodiments of the present method, the metal hydride comprises a compound of the formula $M^1{}_aM^2{}_bH_cR^6{}_{d'}$, where $M^1$ and $M^2$ are independently first and second metals, each $R^6$ in the metal hydride compound is independently a ligand bound to at least one of $M^1$ and $M^2$ by a covalent, ionic or coordination bond, at least one of a' and b' is at least 1, c' is at least 1, and d' is 0 or any integer up to one less than the number of ligand binding sites available on the (a+b) instances of $M^1$ and $M^2$. In certain implementations, the metal hydride comprises a member of the group consisting of lithium aluminum hydride (LAH, as shown in FIGS. 1-2), calcium aluminum hydride, sodium borohydride, aluminum hydride, gallium hydride, and aluminum borohydride.

Figure 3:
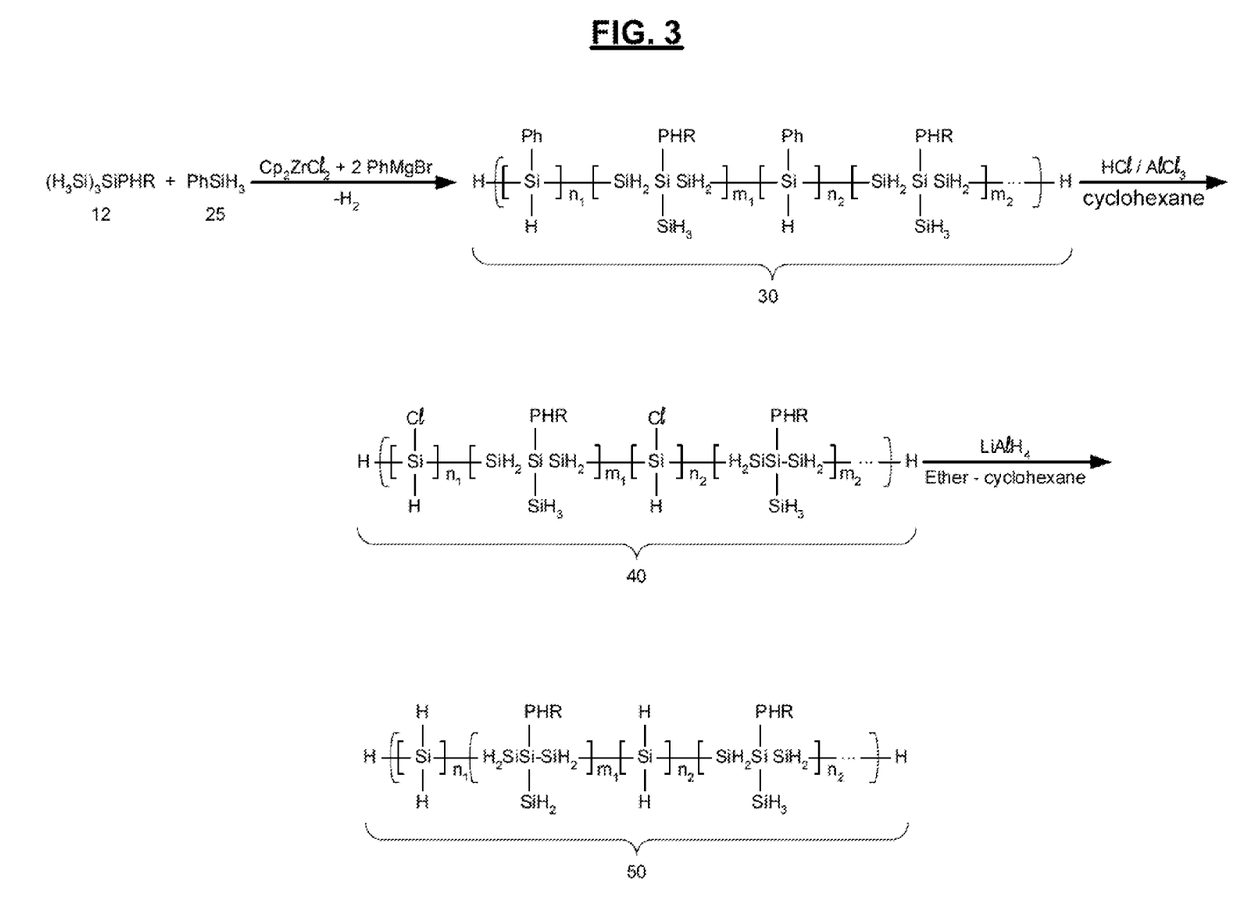
FIG. 3 is a diagram showing an approach for the synthesis of doped polysilanes from doped silanes and arylsilane monomers by catalytic dehydrocoupling, halogenation, and reduction.
Figure 4:
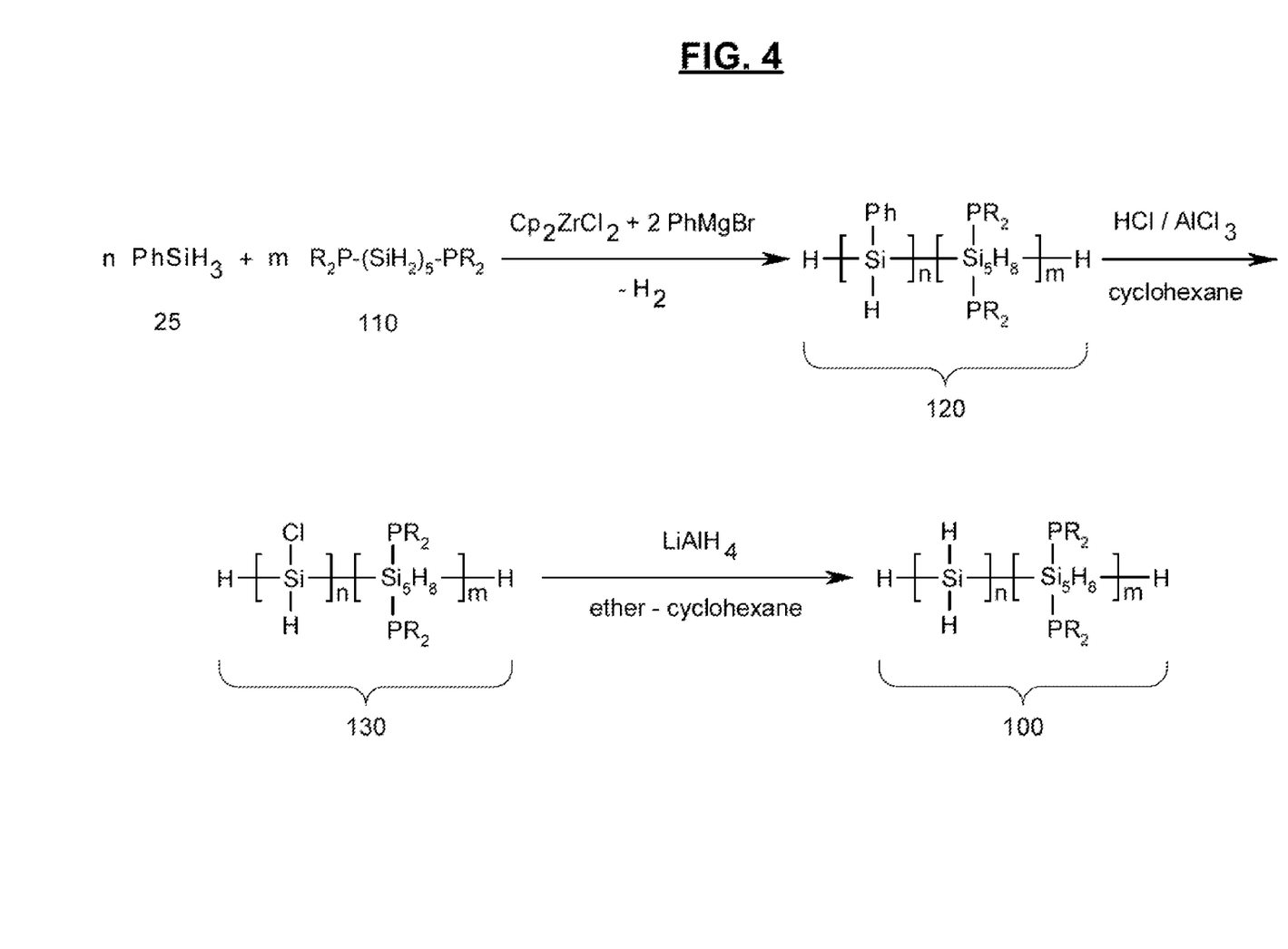
FIG. 4 is a diagram showing an alternative approach for the synthesis of doped polysilanes from an arylsilane monomer and a doped silane by catalytic dehydrocoupling, halogenation, and reduction.

Referring to FIGS. 3-4, the procedure for Lewis acid-catalyzed halogenation (e.g., treatment or reaction of doped polyarylsilane 30 or 120 (respectively formed by catalytic dehydrocoupling of $(H_3Si)_3SiPHR$ 12 and $PhSiH_3$ 25 [FIG. 3], or $PhSiH_3$ 25 and linear doped silane $(H_2Si)_5(PR_2)_2$ 110 [FIG. 4]) with HCl and $AlCl_3$ in an inert organic solvent such as cyclohexane is largely as described in U.S. patent application Ser. No. 10/789,317. However, exemplary variations of the procedure include a halogenation (e.g., chlorination) by bubbling HX gas (e.g., dry HCl) through a solution of doped polyarylsilane 30 or 120 and a Lewis acid for a length of time of from 30 min. to about 6 hours to form polychlorosilane 40 or 130, respectively, and reduction using a metal hydride reducing reagent (not limited to lithium aluminum hydride [LAH], although LAH as shown in FIGS. 3-4 is a preferred metal hydride reducing reagent) for a length of time of from about 1 hour, 2 hours or 4 hours to about 8, 12, or 16 hours (e.g., overnight). Other exemplary metal hydride reducing agents are disclosed in U.S. patent application Ser. Nos. 10/789,317, 10/949,013, 10/950,373 and 10/956,714, the relevant portions of which are incorporated herein by reference. Also, the reagent addition sequence preferably comprises adding a solution of metal hydride (e.g., LAH) in an inert organic solvent (e.g., dry diethyl ether) to a stirred solution of doped polychlorosilane 40 or 130. Workup is generally as described in U.S. patent application Ser. Nos. 10/789,317, 10/949,013, 10/950,373 and 10/956,714, the relevant portions of which are incorporated herein by reference.

The starting material(s) and/or substrates generally include silicon and germanium compounds of the general formula $R^1AH_3$ or $R^1{}_2AH_2$, where A is Si or Ge, and $R^1$ is aryl or substituted aryl. Use of tolylsilane ($CH_3C_6H_4SiH_3$) as a monomer instead of phenylsilane ($PhSiH_3$) may be advantageous for subsequent steps in the doped polysilane synthesis. Tolylsilane (and oligomers thereof) are generally easier to chlorinate (e.g., cleave the C—Si bond with HCl and a Lewis acid such as $AlCl_3$), thereby presumably reducing aromatic impurities in any subsequently synthesized doped polysilane.

In further embodiments of the approach exemplified in FIGS. 3-4 and 6-7, A is independently Si or Ge, each polyarylsilane 30 or 120 may contain a number of subblocks $n_1$-$n_x$ and/or $m_1$-$m_y$, where x and y are independently an integer of from 2 to 12 (preferably from 2 to 8). In addition, linear and/or branched silanes of the general formula $A_kH_{2k+2}$ (where k is from 1 to 12, preferably from 5 to 10 [e.g., for homogeneous synthesis] or from 1 to 4 [e.g., for heterogeneous synthesis]) may be added to the dehydrocoupling reaction mixture to form triblock arylpolysilanes, generally as described herein.

Figure 6:
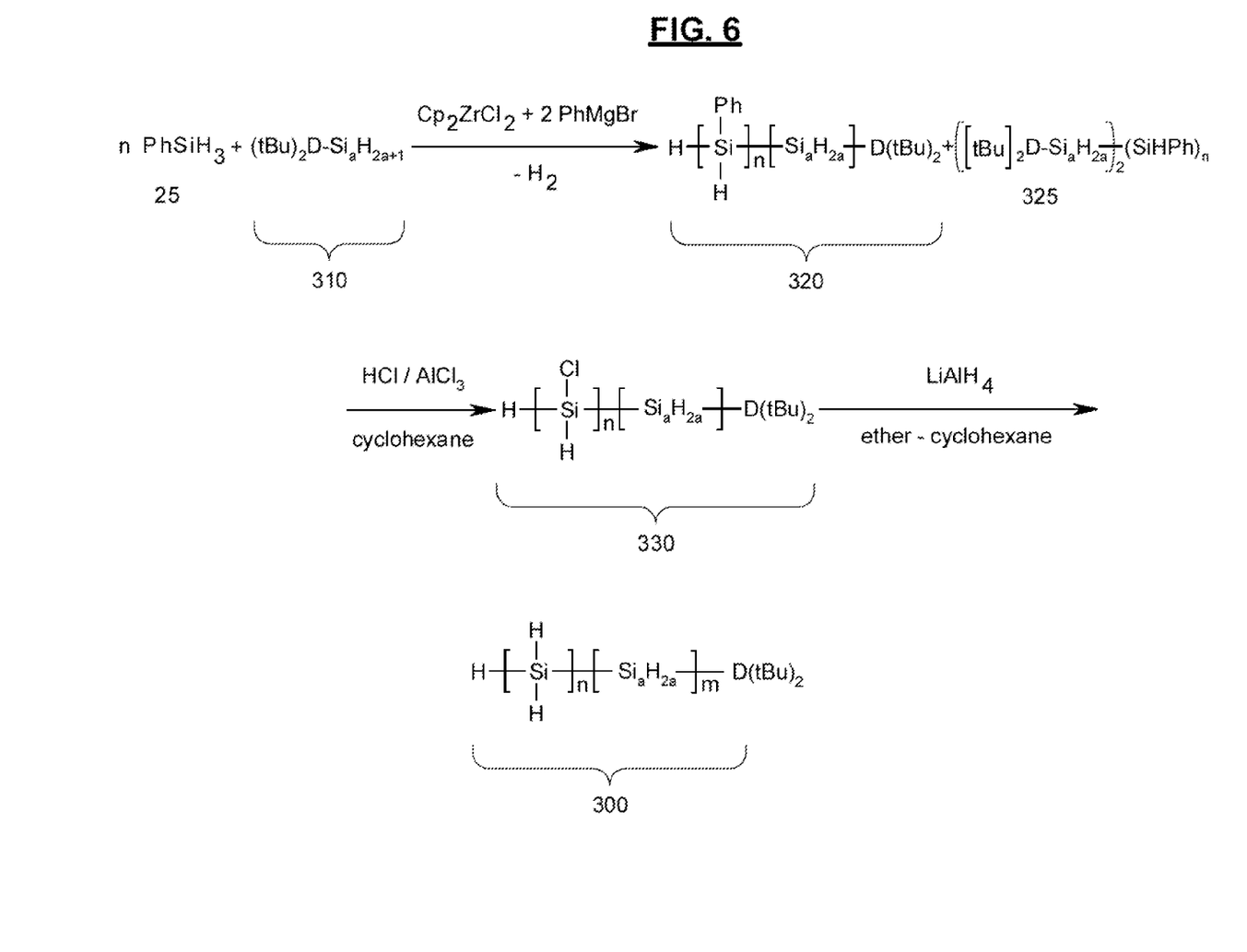
FIG. 6 is a diagram showing an approach for the synthesis of doped polysilanes from arylsilane and doped silane monomers by catalytic dehydrocoupling, halogenation, and reduction.

In another aspect, FIG. 6 shows a scheme for making capped, substantially linear doped oligo- and/or polysilanes, based on catalytic dehydrocoupling (e.g., dehydrocoupling of undoped [aryl]silanes and/or [aryl]germanes with sterically crowded, doped silanes and/or germanes). FIG. 6 shows an exemplary scheme illustrating dehydrocoupling of phenylsilane ($PhSiH_3$) 25 with di-t-butyl(silylated)phosphine 310 to form copolymer or linear/branched end-capped doped poly (phenylsilylene) 320. Generally, some di-capped polymer 325 will be formed as well. The number of A atoms in the polymers 320 and 325 (e.g., the length of the silicon chain) can be controlled by the molar ratio of undoped monomer (e.g., phenylsilane 25) to doped silane capping group. For example, a molar ratio of from 4:1 to about 20:1 may give good results in terms of ink viscosity, dopant concentration, molecular weight (e.g., Mn) uniformity, etc. Linear or branched perhydrosilanes can be substituted for or added to the undoped silane monomer, to provide a greater degree of branching or to possibly increase the average number of silicon atoms in the polymer/oligomer.

The capping effect of di-t-butyl(silylated)phosphine 310 may be most advantageous when a (i.e., the number of A atoms) is relatively small (e.g., 3 or less, such as $SiH_3$). Of course, it may not always be possible to make di-t-butyl (silylated)phosphine 310, so other groups contributing to steric crowding at the dopant atom may be substituted for one or both of the t-butyl groups (e.g., phenyl, tolyl, t-hexyl or 3,3-dimethylbutyl, i-butyl or n-butyl). Such steric crowding may also reduce any rate-limiting effects the dopant atom may have on the dehydrocoupling reaction.

A Third Exemplary Method for Making Doped Oligo- and/or Polysilanes

Figure 7:
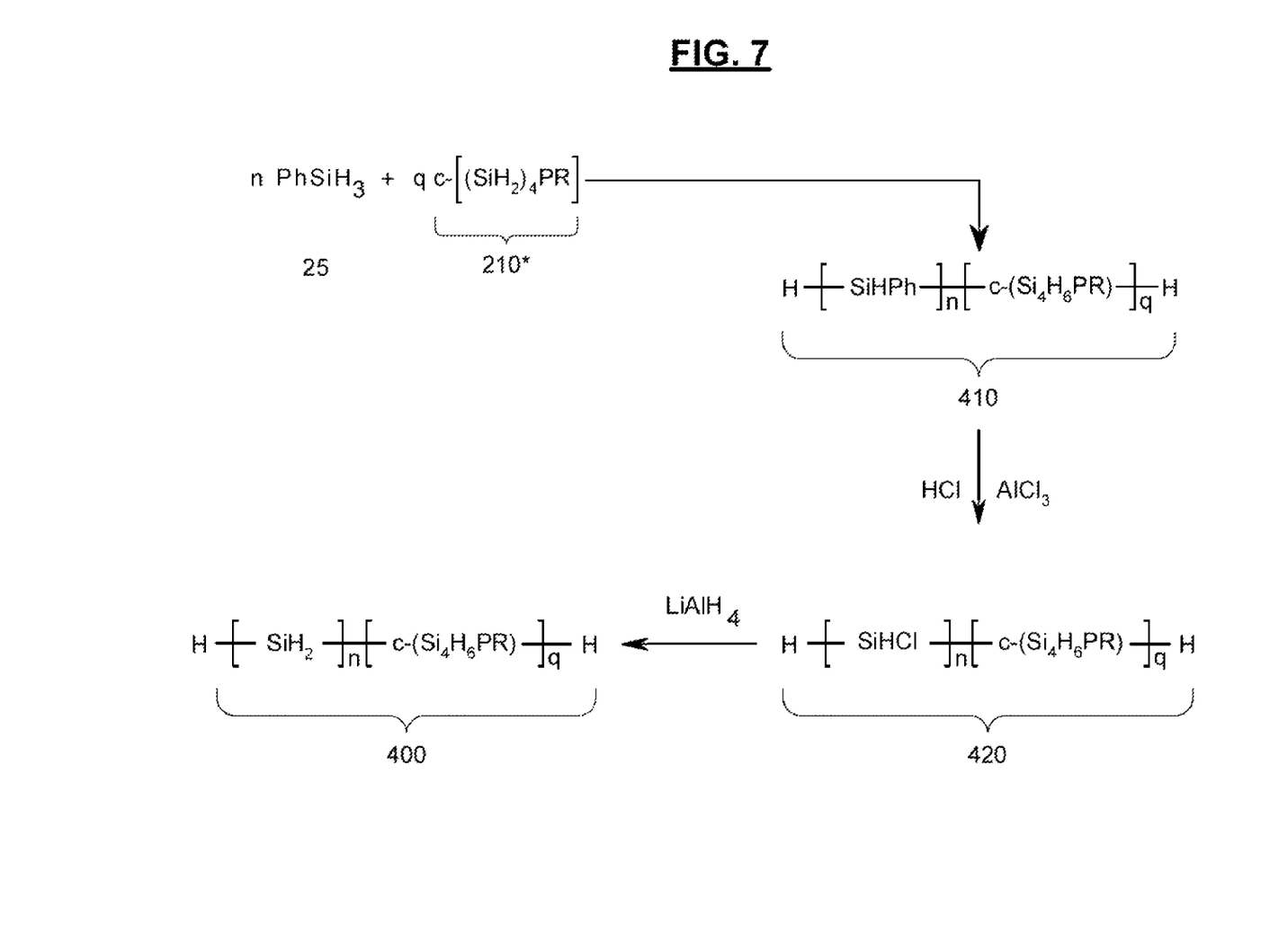
FIG. 7 is a diagram showing an approach for the synthesis of doped poly(cyclo)silanes from arylsilane monomers and doped cyclosilanes by catalytic dehydrocoupling, halogenation, and reduction.

In another aspect, the present invention concerns doped oligo- and/or polysilanes containing both linear and cyclic portions and a method of making the same, based on catalytic dehydrocoupling (e.g., dehydrocoupling of [aryl]silanes and/ or [aryl]germanes with cyclosilanes and/or cyclogermanes), such as the exemplary reaction scheme of FIG. 7. FIG. 7 shows an exemplary scheme illustrating dehydrocoupling of phenylsilane (PhSiH$_3$) with cyclo-Si$_4$H$_8$PR 410 to form copolymer or linear/branched poly(phenylsila)(cyclotetrasilylene[substituted]-phosphine) 420. Generally, the same dehydrocoupling catalyst (e.g., bis[cyclopentadienyl]diphenylzirconium or [Fl$_2$SiMe$_2$]ZrBu$_2$, as shown in FIGS. 1-6) described above may be used for dehydrocoupling arylsilanes with doped cyclosilanes. Linear or branched perhydrosilanes can be substituted for or added to the undoped silane monomer, to provide a greater degree of branching or to possibly increase the average number of silicon atoms in the polymer/oligomer. Also, cyclosilanes with an exocyclic silyl group (e.g., where R=SiH$_3$) are also contemplated for use in the invention.

An Exemplary Composition and/or Ink Containing a Doped Polysilane

A further aspect of the present invention relates to a composition, comprising the present doped polysilane and a solvent in which the doped polysilane is soluble. Preferably, the solvent is one that is easily removed (and/or substantially completely removable) from the composition, and may be selected from the group consisting of linear alkanes, cycloalkanes, polycycloalkanes, (cyclic) siloxanes and fluoroalkanes. The (cyclic) siloxane solvents are generally those that are liquid at ambient temperatures (e.g., 15-30° C.), and may be selected from siloxanes of the formula (R$_3$Si)(OSiR$_2$)$_p$(OSiR$_3$) and cyclosiloxanes of the formula (SiR'$_2$O)$_q$, where p is from 0 to 4, q is from 2 to 6 (preferably from 3 to 5), each R and R' is independently H, C$_1$-C$_6$ alkyl, benzyl or phenyl substituted with from 0 to 3 C$_1$-C$_4$ alkyl groups (preferably R and R' are methyl). The fluoroalkane may be selected from C$_3$-C$_8$ fluoroalkanes substituted with from 1 to (2 m+2) fluorine atoms and that are liquid at ambient temperatures, where m is the number of carbon atoms in the fluoroalkane. More preferably, the solvent may be selected from the group consisting of C$_6$-C$_{12}$ monocycloalkanes and C$_{10}$-C$_{14}$ di- or tricycloalkanes (e.g., decalin). Preferably, the solvent is a C$_6$-C$_{10}$ cycloalkane (e.g., cyclohexane, cycloheptane, cyclooctane, etc.).

In the present ink composition, the doped polysilane is present in an amount of from about 0.001 to about 50%, preferably 0.01 to about 20% (more preferably from about 0.05 to about 10%) by weight or by volume. The present ink composition may further comprise an undoped polysilane in an amount of from about 0.5 to about 50%, about 5 to about 30%, or about 10 to about 20% by weight or by volume. Of course, when the doped polysilane (and, when present, any undoped polysilane) is in a liquid phase at room temperature, it may be used neat if its viscosity (and/or other physical and/or chemical properties) are suitable for printing and/or coating processes. Suitable ink formulations are disclosed in U.S. patent application Ser. Nos. 10/789,274, 10/789,317, 10/949,013, 10/950,373 and 10/956,714, respectively filed on Feb. 27, 2004, Feb. 27, 2004, Sep. 24, 2004, Sep. 24, 2004, and Oct. 1, 2004, the relevant portions of which are incorporated herein by reference.

An Exemplary Method for Making a Doped Semiconductor Film

A further aspect of the invention relates to a method of forming a doped or electrically active semiconductor film from the present composition, comprising the steps of (A) spin-coating or printing the composition onto a substrate (optionally, with simultaneous or immediately subsequent UV irradiation); (B) heating the composition sufficiently to form a doped, amorphous, hydrogenated semiconductor; and (C) annealing and/or irradiating the doped, amorphous, hydrogenated semiconductor sufficiently to at least partially crystallize, reduce a hydrogen content of, and/or electrically activate the dopant in the doped, amorphous, hydrogenated semiconductor, and form the doped or electrically active semiconductor film. Preferably, the method of forming a doped or electrically active semiconductor film comprises printing (e.g., inkjetting) the composition onto a substrate (e.g., a conventional silicon wafer, glass plate, ceramic plate or disc, plastic sheet or disc, metal foil, metal sheet or disc, or laminated or layered combination thereof, any of which may have an insulator layer such as an oxide layer thereon), and/or irradiating the doped, amorphous, hydrogenated semiconductor with a sufficient dose of laser radiation to crystallize and/or electrically activate the doped, amorphous, hydrogenated semiconductor and form an electrically active semiconductor film.

In the present method, it may be advantageous to irradiate the composition during deposition onto the substrate. Generally, as long as the ink composition is irradiated reasonably shortly after deposition (e.g., spincoating), it has a viscosity sufficient to form a film or layer on the substrate that does not bead up, disproportionate or otherwise substantially adversely affect the uniformity of a subsequently formed semiconductor film. Such irradiation of a coated and/or printed film prior to curing may provide further control of the film drying process, e.g., by increasing the viscosity of the ink composition after deposition. For example, the present composition (e.g., prior to deposition) may have a viscosity of from 2.5 to 20 cP, 3 to 12 cP, or any range of values therein. Due to the potential sensitivity of the present polysilanes to air, such deposition and (optional) irradiation should be conducted in an inert atmosphere.

Suitable methods for forming a semiconductor film are disclosed in U.S. patent application Ser. Nos. 10/789,274, 10/949,013, 11/084,448 and 11/203,563, respectively filed on Feb. 27, 2004, Sep. 24, 2004, Mar. 18, 2005 and Aug. 11, 2005, the relevant portions of which are incorporated herein by reference. In the present case, the doped polysilane ink composition may further include a (cyclo)silane and/or hetero(cyclo)silane as described in U.S. patent application Ser. Nos. 10/789,274, 10/949,013, 11/084,448 and 11/203,563. The first heating and/or annealing step may comprise (i) "soft" curing the printed or coated ink composition, generally at a temperature of ≦200° C., ≦150° C., ≦120° C. or any maximum temperature in that range, sufficiently to remove volatile components (e.g., solvent, volatile silane compounds, etc.) and/or to further polymerize the doped silane film, and (ii) "hard" curing the film, generally at a temperature of ≦600° C., ≦500° C., ≦450° C. or any maximum temperature in that range, sufficiently to form a doped, hydrogenated, amorphous silicon film. Due to the potential sensitivity of the present polysilanes to air, such curing (e.g., "soft" and/or "hard" curing) should be conducted in an inert atmosphere. Generally, to obtain the most commercially valuable electrical activity and/or characteristics, the film is crystallized by heating in a furnace or irradiating with a dose of laser radiation sufficient to partly or substantially completely crystallize the doped, hydrogenated, amorphous silicon film (e.g., form a polycrystalline silicon film). The use of laser radiation for crystallization advantageously includes a further annealing step to reduce the hydrogen content of the doped, hydrogenated, amorphous silicon film prior to laser irradiation.

Coating may comprise spin coating, inkjetting, dip-coating, spray-coating, slit coating, extrusion coating, or meniscus coating the ink composition onto a substrate. Preferably, coating comprises spin coating. Printing may comprise inkjetting or gravure, flexographic, screen or offset printing the ink in locations on the substrate corresponding to active transistor regions. After drying and/or heating the printed/coated film to remove any solvents and/or cure the film, and optionally irradiating the film (e.g., to fix the silanes to the substrate and/or to each other), the resulting semiconductor film/layer generally has an amorphous morphology, and before further processing, it is generally annealed (e.g., to reduce the hydrogen content of the polysilane) and crystallized (e.g., by heating or by laser irradiation; see, e.g., U.S. patent application Ser. Nos. 10/950,373 and 10/949,013, each of which was filed on Sep. 24, 2004, the relevant portions of which are incorporated herein by reference). In many cases, such crystallization will also activate at least some of the dopant.

One may also induce crystallization (in addition to activating some or all of the dopant) using conventional metal-promoted (re)crystallization. Suitable metal-based crystallization promoters and processes for their use in crystallizing an amorphous semiconductor film (e.g., as formed from semiconductor nanoparticles containing Si and/or Ge) may be disclosed in copending application Ser. No. 10/339,741, filed Jan. 8, 2003 and entitled "Nanoparticles and Method for Making the Same", now U.S. Pat. No. 7,078,276, the relevant portions of which are incorporated herein by reference.

CONCLUSION/SUMMARY

As described above, doped oligo- and polysilanes and -germanes suitable for semiconductor inks can be synthesized by dehydrocoupling of silyl- and/or germylphosphines, or silyl- and/or germylboranes, optionally in the presence of perhydrosilanes and perhydrogermanes. Alternatively, such doped oligo- and polysilanes and -germanes may be synthesized by dehydrocoupling of arylhydrosilanes and arylhydrogermanes with such silyl- and/or germyl-phosphines or -boranes, followed by halogenative cleavage of the aryl groups and metal hydride reduction to yield doped perhydrosilanes and perhydrogermanes. Such synthesis allows for tuning of the ink properties (e.g., viscosity, boiling point, and surface tension) and for deposition of silicon films or islands by spincoating, inkjetting, dropcasting, etc., with or without the use of UV irradiation. For example, the dopant level in the ink compositions can be controlled by the ratio of dopant compound (e.g., the silyl- and/or germylphosphine or -borane) to perhydro- or arylhydrosilane or -germane in the dehydrocouping reaction.

The inks can be used for production of amorphous and polycrystalline silicon, germanium, or silicon-germanium films by spincoating or inkjet printing, followed by curing at 400-500° C. and (optionally) laser-, heat-, or metal-induced crystallization (and/or dopant activation, when dopant is present; also see, e.g., U.S. application Ser. No. 11/246,014, filed concurrently herewith and incorporated herein by reference in its entirety). Highly doped films may be used to make contact layers in MOS capacitors, TFTs, diodes, etc. Lightly doped films may be used as semiconductor films in MOS capacitors, TFTs, diodes, etc.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

What is claimed is:

1. A doped polysilane of the formula H-$[A_aH_b(DR_x)_m]_q$-$[(A_cH_dR^1_e)_n]_p$—H, where each instance of A is independently Si or Ge; D is B, P, As or Sb; each instance of R is independently alkyl, alkylene, aralkyl, substituted aralkyl, aryl, arylene or substituted aryl, and when an instance of x=2, the two R groups may form a ring together with D; q is at least 1, but $q \geq 2$ when p=0; each of the q instances of a is independently at least 1; each of the q instances of b is independently an integer of from 1 to 2a; each of the q instances of m is an integer of from 1 to a; each of the q*m instances of x is independently 1 or 2; each instance of $R^1$ is independently H, -$A_fH_{f+1}R^2_f$, halogen, aryl or substituted aryl; each of the p instances of n is independently at least 1; each of the p*n instances of c is independently an integer of at least 1; each of the p*n instances of d is independently an integer of from c to 2c; each of the p*n instances of e is independently an integer of from 0 to c; and the sum of the p instances of n*c$\geq$4 when q=1.

2. The doped polysilane of claim 1, wherein R is, alkyl or aryl.

3. The doped polysilane of claim 2, wherein R is $C_1$-$C_6$ alkyl, phenyl, or tolyl.

4. The doped polysilane of claim 3, wherein R is $C_1$-$C_4$ alkyl.

5. The doped polysilane of claim 3, wherein a is an integer of from 2 to 6.

6. The doped polysilane of claim 3, wherein b is (2a–2–m), (2a–2), (2a–m), or 2a.

7. The doped polysilane of claim 1, having an average number of A atoms of at least 15 according to or as calculated from a number average molecular weight Mn of the doped polysilane.

8. The doped polysilane of claim 7, wherein A is Si.

9. The doped polysilane of claim 1, wherein D is B or P.

10. The doped polysilane of claim 1, wherein p is 0.

11. The doped polysilane of claim 1, wherein $R^1$ is phenyl, tolyl, Cl or H; and n*p $\geq$4.

12. The doped polysilane of claim 11, wherein $R^1$ is phenyl or H, and n*p has an average value of at least 10.

13. The doped polysilane of claim 12, wherein $R^1$ is H.

14. A composition, comprising:
a) the doped polysilane of claim 1; and
b) a solvent in which the doped polysilane is soluble.

15. The composition of claim 14, wherein said solvent is selected from the group consisting of linear alkanes, cycloalkanes, polycycloalkanes, (cyclic) siloxanes, and fluoroalkanes.

16. The composition of claim 15, wherein said solvent is selected from the group consisting of $C_6$-$C_{12}$ monocycloalkanes and $C_{10}$-$C_{14}$ di- or tricycloalkanes.

17. The composition of claim 15, wherein said solvent is a $C_6$-$C_{10}$ cycloalkane.

18. The composition of claim 14, wherein the doped polysilane is present in the composition in an amount of from about 0.0001 to about 50% by weight or by volume.

19. The composition of claim 14, further comprising an undoped polysilane present in an amount of from about 0.5 to about 50% by weight or by volume.

20. A doped polysilane of the formula H-$[A_aH_b(DR_x)_m]_q$-$[(A_cH_dR^1_e)_n]_p$—H, where each instance of A is independently Si or Ge; D is B, P, As or Sb; each instance of R is $C_1$-$C_4$ alkyl; q is at least 1, but q$\geq$2 when p=0; each of the q instances of a is independently at least 1; each of the q instances of b is independently an integer of from 1 to 2a; each of the q instances of m is an integer of from 1 to a; each of the q*m instances of x is independently 1 or 2; each instance of $R^1$ is independently -$A_fH_{f+1}R^2_f$, halogen, aryl or substituted aryl; each of the p instances of n is independently at least 1; each of the p*n instances of c is independently an integer of at least 1; each of the p*n instances of d is independently an integer of from c to 2c; each of the p*n instances of e is independently an integer of from 0 to c; and the sum of the p instances of n*c>4 when q=1.

21. The doped polysilane of claim 20, wherein a is an integer of from 1 to 6.

22. The doped polysilane of claim 21, wherein when x=1, b is 2a or 2a−2, and when x=2, b is 2a+1 or 2a−1.

23. The doped polysilane of claim 20, wherein A is Si.

24. The doped polysilane of claim 20, wherein b is 2a or 2a−1, and m=1.

25. The doped polysilane of claim 20, wherein p is an integer of at least 1, d is 2c or 2c−2, and e=0.

26. The doped polysilane of claim 20, having an average number of A atoms of at least 10 according to or as calculated from a number average molecular weight Mn of the doped polysilane.

27. The doped polysilane of claim 20, wherein p is an interger of at least 1, and $R^1$ is phenyl, totyl, Cl or H.

28. A doped polysilane of the formula H-[$A_aH_b(DR_x)_m$]$_q$-[($A_cH_dR^1_e)_n$]$_p$—H, where each instance of A is independently Si or Ge; D is B, P, As or Sb; each instance of R is independently H, -$A_fH_{2f+1}$(where f is an interger≦4), $C_1$-$C_6$ alkyl; phenyl, or tolyl; is at least 1, but q≧2 when p=0; each of the q instances of a is independently at least 1; each of the q instances of b is independently (2a−2−m), (2a−2), (2a−m), or 2a; each of the q instances of m is an integer of from 1 to a; each of the q*m instances of x is independently 1 or 2; each instance of $R^1$ is independently H, -$A_fH_{f+1}R^2_f$, halogen, aryl or substituted aryl; each of the p instances of n is independently at least 1; each of the p*n instances of c is independently an integer of at least 1; each of the p*n instances of d is independently an integer of from c to 2c; each of the p*n instances of e is independently an integer of from 0 to c; and the sum of the p instances of n*c≧4 when q=1.

29. The doped polysilane of claim 28, wherein a is an integer of from 1 to 6.

30. The doped polysilane of claim 29, wherein when x=1, b is 2a or 2a−2, and when x=2, b is 2a+1 or 2a−1.

31. The doped polysilane of claim 28, having an average number of A atoms of at least 10 according to or as calculated from a number average molecular weight Mn of the doped polysilane.

32. The doped polysilane of claim 28, wherein p is an integer of at least 1, and $R^1$ is phenyl, tolyl, Cl or H.

33. The doped polysilane of claim 28, wherein A is Si.

34. The doped polysilane of claim 28, wherein b is 2a or 2a−1, and m=1.

35. A doped polysilane of the formula H-[$A_aH_b(DR_x)_m$]$_q$-H, where each instance of A is independently Si or Ge; D is B, P, As or Sb; each instance of R is independently H, -$A_fH_{f+1}R^2_f$ (where $R^2$ is H, halogen, aryl or substituted aryl and f is an integer≦6), alkyl, alkylene, aralkyl, substituted aralkyl, halogen, aryl, arylene or substituted aryl, and when an instance of x =2, the two R groups may form a ring together with D; q is an integer≧2; each of the q instances of a is independently at least 1; each of the q instances of b is independently an integer of from 2 to 2a; each of the q instances of m is an integer of from 2 to a; and each of the q*m instances of x is independently 1 or 2.

36. The doped polysilane of claim 35, wherein R is alkyl or aryl.

37. The doped polysilane of claim 36, wherein R is $C_1$-$C_4$ alkyl, phenyl or tolyl.

38. The doped polysilane of claim 35, wherein b is (2a−2−m), (2a−2), (2a−m), or 2a.

39. The doped polysilane of claim 35, wherein A is Si.

40. The doped polysilane of claim 35, wherein when x=1, b is 2a or 2a−2, and when x=2, b is 2a+1 or 2a−1.

41. The doped polysilane of claim 35, wherein $R^1$ is H or X.

42. A composition, comprising:
a) a doped polysilane of the formula H-[$A_aH^b(DR_x)_m$]$_p$-[($A_cH_dR^1_e)_n$]$_p$-H, where each instance of A is independently Si or Ge; D is B, P, As or Sb; each instance of R is independently H, -$A_fH_{f+1}R^2_f$ or -$A_fH_fR^2_f$ (where $R^2$ is H, halogen, aryl or substituted aryl, and f is an integer≦6), alkyl, alkylene, aralkyl, substituted aralkyl, halogen, aryl, arylene or substituted aryl, and when an instance of x=2, the two R groups may form a ring together with D; q is at least 1, but q≧2 when p=0; each of the q instances of a is independently at least 1; each of the q instances of b is independently an integer of from 1 to 2a; each of the q instances of m is an integer of from 1 to a; each of the q*m instances of x is independently 1 or 2; each instance of $R^1$ is independently H, -$A_fH_{f+1}R^2_f$, halogen, aryl or substituted aryl; each of the p instances of n is independently at least 1; each of the p*n instances of c is independently an integer of at least 1; each of the p*n instances of d is independently an integer of from c to 2c; each of the p*n instances of e is independently an integer of from 0 to c; and the sum of the p instances of n*c≧4 when q=1;
b) a solvent in which the doped polysilane is soluble; and
c) an undoped polysilane present in an amount of from about 0.5 to about 50% by weight or by volume.

43. The composition of claim 42, wherein said solvent is selected from the group consisting of linear alkanes, cycloalkanes, polycycloalkanes, (cyclic) siloxanes, and fluoroalkanes.

44. The composition of claim 43, wherein said solvent is selected from the group consisting of $C_6$-$C_{12}$ monocycloalkanes and $C_{10}$-$C_{14}$ di- or tricycloalkanes.

45. The composition of claim 42, wherein the doped polysilane is present in the composition in an amount of from about 0.0001 to about 50% by weight or by volume.

* * * * *